US006700012B2

(12) United States Patent
Ayers

(10) Patent No.: US 6,700,012 B2
(45) Date of Patent: Mar. 2, 2004

(54) ANTIHISTAMINIC PIPERIDINE DERIVATIVES AND INTERMEDIATES FOR THE PREPARATION THEREOF

(75) Inventor: Timothy A. Ayers, Bridgewater, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 10/104,311

(22) Filed: Mar. 22, 2002

(65) Prior Publication Data

US 2002/0099090 A1 Jul. 25, 2002

Related U.S. Application Data

(62) Division of application No. 09/723,799, filed on Nov. 28, 2000, now abandoned, which is a continuation of application No. 09/344,024, filed on Jun. 25, 1999, now abandoned.
(60) Provisional application No. 60/155,244, filed on Jul. 2, 1998.

(51) Int. Cl.[7] .................... C07C 69/612; C07C 69/74
(52) U.S. Cl. ............... 560/81; 560/76; 560/101; 560/124; 560/127; 562/489; 562/491; 562/506; 562/509
(58) Field of Search ................ 560/76, 81, 101, 560/124, 127; 562/489, 491, 506, 509

(56) References Cited

U.S. PATENT DOCUMENTS

| | | | |
|---|---|---|---|
| 3,839,431 A | | 10/1974 | Sheehan et al. |
| 3,898,271 A | * | 8/1975 | Sheehan et al. ............... 560/57 |
| 3,965,257 A | | 6/1976 | Carr et al. |
| 3,978,071 A | | 8/1976 | Nakanishi et al. |
| 4,028,404 A | | 6/1977 | Bays et al. |
| 4,105,790 A | | 8/1978 | Hughes et al. |
| 4,254,129 A | | 3/1981 | Carr et al. |
| 4,254,130 A | | 3/1981 | Carr et al. |
| 4,285,957 A | | 8/1981 | Carr et al. |
| 4,285,958 A | | 8/1981 | Carr et al. |
| 4,381,398 A | | 4/1983 | Takizawa et al. |
| 4,407,823 A | | 10/1983 | Kirsch et al. |
| 4,434,182 A | | 2/1984 | Cruickshank et al. |
| 4,452,985 A | | 6/1984 | Santilli et al. |
| 4,550,116 A | | 10/1985 | Soto et al. |
| 4,686,018 A | | 8/1987 | Jacques |
| 4,990,658 A | | 2/1991 | Stahly et al. |
| 5,214,047 A | | 5/1993 | Ostersehlt et al. |
| 5,581,011 A | * | 12/1996 | D'Ambra ................ 560/8 |
| 5,654,433 A | | 8/1997 | King et al. |

FOREIGN PATENT DOCUMENTS

| | | | |
|---|---|---|---|
| AU | 20150/88 | * | 2/1989 |
| AU | 38608/93 | | 5/1993 |
| DE | 2134743 | | 7/1971 |
| DE | 2432410 | | 1/1975 |
| DE | 2653635 | | 6/1977 |
| DE | 3010752 | | 10/1980 |
| DE | 3730718 | | 3/1989 |
| EP | 0301421 | | 7/1987 |
| EP | 0571253 | | 11/1993 |
| EP | 0723958 | | 7/1996 |
| JP | 58-008081 | * | 1/1983 |
| JP | 60-115547 | * | 6/1985 |
| WO | WO 95/00480 | | 1/1995 |
| WO | WO 95/00482 | | 1/1995 |
| WO | WO 96/35667 | | 11/1996 |

OTHER PUBLICATIONS

Ali A. Khalaf et al., Modern Friedel–Crafts Chemistry XIII. Intra–and intermolecular Cyclization of Some Carbonyl Derivatives under Friedel–Crafts Conditions., Bull Soc. Chim. Fr. (1984, pp. 285–291).

Antonio G. Gonzalez et al., A Synthesis of 3–Hydroxymethyl–6–Methylbenzofuran, Heterocycles (1992, pp. 1311–1315, vol. 34, No. 7.

B.R. Colah et al., Synthesis of Thiazolyl Derivatives of Possible Therapeutic Value ( Antiinflammatory Agents –III) Bull Haff Instt (1977, pp. 20–22, vol. 5, No. 1.)

Catherine Schaal, Synthese. Extension des relations lineaires d'enthalpie libre aux parametres de resonance magnetique nucleaire, Bull Soc. Chim. Fr. (1971, pp.3064–3070, Vol. 8).

Charles R. Davis et al., Tetramethyl 1,1,4,4–Cyclohexane-tetracarboxylate: Preparation and Conversion to Key Precursors of Fluorinated, Stereochemically Defined Cyclohexanes, J. Org. Chem. (1993, pp. 6843–6850, vol. 58).

D. R. Shridhar et al., Antiinflammatory Agents: Part VIII Synthesis of Some 3–Aryl–2H–1, 4–Benzo–xazine–6–Alkanoic Acids & Methyl4–(6–Chloro–/6–nitro–2H–1, 4–Benzoxazin–3–yl)–Phenylacetates, Indian Journal of Chemistry (1983, pp. 297–299, vol. 22B).

(List continued on next page.)

Primary Examiner—Ceila Chang
(74) Attorney, Agent, or Firm—James W. Bolcsak

(57) ABSTRACT

This invention relates to compounds of the formula:

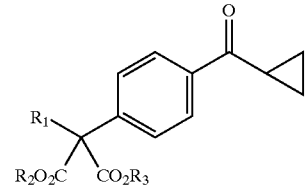

wherein $R_1$ is H or $C_1-C_6$ alkyl and the $C_1-C_6$ alkyl moiety is straight or branched;

$R_2$ and $R_3$ are each independently $C_1-C_6$ alkyl and the $C_1-C_6$ alkyl moiety is straight or branched; or stereoisomers thereof.

2 Claims, No Drawings

OTHER PUBLICATIONS

D. W. McPherson et al., Radiolabeling of Proteins with Radioisotopes of Copper Using p–Carboxyalkylphenylglyoxal bis–(4N–Methylthiosemicarbazone) (TSC) Bifunctional Chelates, Journal of Labelled Compounds and Radiopharmaceuticals.

Danielle Roche et al., Synthesis of New Cyclopropylvinyl Sulfones, Sulfur Letters (1992, pp. 127–133, vol. 15(3)).

Dennis D. Tanner et al., On the Mechanism of the Free–Radical Reactions of Cyanogen and Cyanogen Chloride with Hydrocarbon Substrates, Journal of the American Chemical Society (1969, pp. 3028–3034, vol. 91(11).

Frank H. Stodla, Base–Catalyzed Preparation of Methyl and Ethyl Esters of Carboxylic Acids, Journal Organic Chemistry, (1964, pp. 1964, pp. 2490–2491, vol. 29).

G. Rovnyak et al., Synthesis and Antiinflammatory Activities of (alpha–Cyclopropyl–p tolyl) acetic Acid and Related Compounds, Journal of Medicinal Chemistry, (1973, pp.487–490, vol. 16, No. 5).

H. Auterhoff, Tubingen et al., 3–Amino–6–Formyl–1,2–Dihydro–as–triazin (4), Archiv der Pharmazie (1973, pp. 807–813, vol. 306).

Hak Jin Kim et al., One–Pot Synthesis of alpha–Chloroketones From Secondary Benzylic Alcohols Using m–Chloroperbenzoic Acid/HCl/DMF System, Synthetic Communications (1990, pp. 1625–1629, vol. 20, No. 11).

Heikki Ruotsalainen et al., The Aluminum Chloride Catalyzed Reactions of 3–Chloropropionyl Chloride with Monoalkybenzenes and Biphenyl and the Influence of 4'–Alky and 4'–Substituents of the Acid–Catalyzed Methanolysis of 2–Phenyloxetane, Suomen Kemistilehti (1970, pp. 91–97, vol. 43, No. 2).

Herbert C. Brown et al., A Convenient Procedure for the Quantitaties Conversion of Reactive Alcohols and Olefins into the Corresponding Chlorides, Journal of Organic Chemistry, (1966, pp. 1090–1093, vol. 31).

J. F. Fauvarque et al., Nickel Catalysed Electrochemistry of Anti–Inflammatory agents. Part I –Synthesis of Aryl–2 Propionic Acids, Under Galvanostic Conditions, Journal of Applied Electrochemistry, (1988, pp. 109–114, vol. 18).

John M. Kane et al., The reactions of Thiosemicarbazides and 5–Halovalerophenones , Heterocycl. Chem. (1988, pp. 1471–1474, vol. 25, No. 5).

Joseph H. Boyer, Oxidative Assistance in the Conversion of alpha–Iodoketones to alpha–Kelots, Synthesis (1988, pp. 980–981, Issue No. 12).

Juan C. Jaen et al., "Synthesis of the enantiomers of reduced haloperidol", Pharm. Res., (1991, CA115(15); 158935m,).

Kanji Omura et al., Oxidation of Alcohols by "Activated" Dimethyl Sulfoxide. A Preparative, Steric and Mechanistic Study, Tetrahedron (1978, pp. 1651–1660, vol. 34).

Keiji Itoh et al., Preparation and Reactivities of (n3–1–and 2–Trimethylsiloxyallyl)Fe(C0)2NO Complexes,. The Chemical Society of Japan (1991, pp. 2965–2977, vol. 64).

Kwang–Ting Liu et al., Electronic and Steric Effects on the Solvation at the Transition State in the Solvolysis of Some Tertiary Benzylic Chlorides, Tetrahedron Letters (1992, pp. 6499–6502, vol. 33, No. 43).

Laszlo Tuke et al., Reactions of Trialky Phosphites with alpha–Halogeno–Ketones., J. Chem. Research (1978, pp. 155–156, vol. 5).

Madesclaire et al, Communications, Synthesis (1981, pp. 828–829, vol. 10).

Minoru Uchida et al., Studies on Gastric Antiulcer Active Agents, III. Synthesis of 1–Substituted 4–(5–Tetrazolyl)thio–1–butanones and Related Compounds, Chem. Pharm. Bull (1989, pp. 958–961, vol. 37, No. 4).

Nagabushanam Kalyanam et al., Remarkable Structural Effects in the Intramolecularly Assisted Hydrolysis of Aryl Chloroalkyl Ketones, Journal Chem. Soc., Chem. Commun. (1987, pp. 1028–1029, vol. 13).

Norio Kimura et al., Mechanistic Evaluation of Dissociative Electron–Transfer and Nucleophilic Substitution Reactions, Journal Am. Chem. Soc. (1994, pp. 4087–4088, vol.

Noriyoshi Masuoka et al., Color Reaction of Sugars with Cysteine, I. Isolation and Chemical Structure of a Pigment Product, Physiol. Chem. & Physics (1981, pp. 124–152, vol. 13).

P. W. Heidbuchel, Ethanolysis of Ortho–, Meta–, and Para-substituted Phenylacetyl Chlorides, Bull. Soc. Chim. Belges. (1968, pp. 149–152, vol. 77).

Reynold C. Fuson et al., A Comparison of the Reactions of Mesityl Cyclopropyl Ketone and Mesityl Propenyl Ketone, Reactions of Mesityl Cyclopropyl and Ketones (1948, pp. 3255–3257, vol. 70).

Richard J. Sundberg et al., Preparation of 2–Aryl and 2–Aryloxymethyl Imidazol[1,2–alpha]pyridines and Related Compounds, J. Heterocycl. Chem. (1988, pp. 129–137, vol. 25, No. 1).

Robert Thornton Morrison et al., Oxidation of Alcohols, Organic Chemistry (1973, p. 528).

Rovnyak et al., Synthesis and Antiinflammatory Activities of (alpha–Cyclopropyl–p–tolyl) acetic Acid and Related Compounds, Journal of Medicinal Chemistry (1973, pp. 487–490, vol. 16, No. 5).

Schaal C., Extension of Linear Free Enthalpy Relationships to Nuclear Magnetic Resonance Parameters., Bull. Soc. Chim. Fr. (1971, pp. 3064–3070, Issue No. 8).

Shridhar, et al, Organic Chemistry Including Medicinal Chemistry, Indian Journal of Chemistry (1982, pp. 602–604, vol. 21B No. 6).

Stanley J. Cristol et al., Stereochemistry and Mechanisms of Cyclopropane Ring Cleavage. , Journal Organic Chemistry, (1971, pp. 2773–2776, vol. 236).

T. M. Chen et al., Determination of the Metabolites of Terfenadine in Human Urine by Thermospray Liquid Chromatography–mass Spectrometry, Journal of Pharmaceutical & Biomedical Analysis (1992, pp. 929–933, vol. 9, Nos. 10–12).

Thomas Hogberg et al., Cyanide as an Efficient and Mild Catalyst in the Aminolysis of Esters, J. Org. Chem. (1987, pp. 2033–2036, vol. 52).

Tsuyoshi Okamoto et al., Preparation of Aromatic Iodoacetyl Derivatives by Direct Iodination with a Potassium Iodide–Potassium Iodate–Sulfuric Acid System, The Chemical Society of Japan (1992, pp. 1731–1733, vol. 65, No. 6).

A Guide to the Chemical Basis of Drug Design, Systematic Drug Development and Rational Research Methods (p. 15) Alfred Burger (1984).

Journal of Organic Chemistry (1985, pp. 5446–5448, vol. 50 (25).

Journal of the Chemical Society, Dalton Trans., (1982, pp. 1091–1097).

* cited by examiner

ANTIHISTAMINIC PIPERIDINE DERIVATIVES AND INTERMEDIATES FOR THE PREPARATION THEREOF

RELATED U.S. APPLICATION DATA

This application is a divisional of U.S. patent application Ser. No. 09/723,799 (filed Nov. 28, 2000) now abandoned, which is a continuation of U.S. patent application Ser. No. 09/344,024 (filed Jun. 25, 1999), now abandoned, which claimed benefit of provisional application 60/155,244 (filed Jul. 2, 1998) now abandoned, which applications are hereby incorporated by reference.

BACKGROUND OF THE INVENTION

This invention relates to novel piperidine derivatives of formula (I) and a process for the preparation thereof.

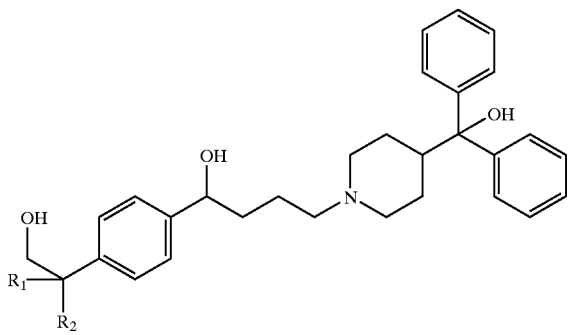

I wherein $R_1$ is H or $C_1$–$C_6$alkyl wherein the $C_1C_6$alkyl moiety is straight or branched;

$R_2$ is —COOH or —COOalkyl wherein the alkyl moiety has from 1 to 6 carbon atoms and is straight or branched; or stereoisomers or pharmaceutically acceptable acid addition salt thereof.

Terfenadine, α-[4-(1,1-dimethylethyl)phenyl]-4-(hydroxydiphenylmethyl)-1-piperidinebutanol, is a known antihistaminic agent which is currently available commercially under the name Seldane® with a recommended dosage of 60 mg b.i.d. (See PHYSICIAN'S DESK REFERENCE, 52nd Edition, 1998, pp.1238–1244, Medical Economics Data, a division of Medical Economics Company, Inc. Montvale, N.J.). Terfenadine is disclosed in U.S. Pat. No. 3,878,217, issued Apr. 15, 1975. Sorken and Heel have provided a review of the pharmacodynamic properties and therapeutic efficacy of terfenadine [*Drugs* 29, 34–56 (1985)].

Terfenadine undergoes extensive (99%) first pass metabolism to two primary metabolites (fexofenadine) and an inactive dealkylated metabolite. Fexofenadine, a.k.a. 4-[1-hydroxy-4-[4-(hydroxydiphenyilmethyl)-1-piperidinyl]butyl-α,α-dimethyl-benzeneacetic acid, has been disclosed as an antihistaminic agent having oral activity in U.S. Pat. No. 4,254,129, issued Mar. 3, 1981. It is currently available commercially under the name Allegra® (See PHYSICIAN'S DESK REFERENCE, 52nd Edition, 1998, pp.1189–1190, Medical Economics Data, a division of Medical Economics Company, Inc. Montvale, N.J.).

SUMMARY OF THE INVENTION

An object of the present invention is to provide novel piperidine derivatives of formula (I) useful for the treatment of allergic disorders. It is a further object to provide a process for the preparation of said derivatives and to provide novel intermediates useful for preparation of the same.

Additionally, it is an object of the present invention to provide a method of treating a patient suffering from an allergic disorder comprising administering to said patient an effective antiallergic amount of a compound of formula (I).

Furthermore, it is an object of the present invention to provide a composition comprising an assayable amount of a compound of formula (I) in admixture or otherwise in association with one or more pharmaceutically acceptable carriers or excipients.

Another object of the present invention is to provide novel processes for the preparation of intermediates useful for the synthesis of fexofenadine and related compounds.

Upon further study of the specification and appended claims, further objects and advantages of this invention will become apparent to those skilled in the art.

DETAILED DESCRIPTION OF THE INVENTION

Compounds of the formula (I) can be prepared using techniques and procedures well known and appreciated by one of ordinary skill in the art.

As used herein, straight or branched alkyl groups having from 1 to 6 carbon atoms as referred to herein are methyl, ethyl, n-propyl, isopropyl, n-butyl, sec-butyl, isobutyl, tert-butyl, and straight- and branched-chain pentyl and hexyl.

The piperidine derivatives of the formula (I) can form pharmaceutically acceptable salts. Pharmaceutically acceptable acid addition salts of the compounds of this invention are those of any suitable inorganic or organic acid. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranillic, cinnamic, salicyclic, 4-aminosalicyclic, 2-phenoxybenzoic, 2-acetoxybenzoic, and mandelic acid, sulfonic acids, such as, methanesulfonic, ethanesulfonic and β-hydroxyethanesulfonic acid. Non-toxic salts of the compounds of the above-identified formula formed with inorganic or organic bases are also included within the scope of this invention and include, for example, those of alkali metals, such as, sodium, potassium and lithium, alkaline earth metals, for example, calcium and magnesium, light metals of group IIIA, for example, aluminum, organic amines, such as, primary, secondary or tertiary amines, for example, cyclohexylamine, ethylamine, pyridine, methylaminoethanol and piperazine. The salts are prepared by conventional means, as for example, by treating a piperidine derivative of formula (1) with an appropriate acid or base.

The novel process for preparing the piperidine derivatives of formula (I) is set forth in Scheme A. in Scheme A, $R_1$, and $R_2$ are $C_1$–$C_6$alkyl wherein the $C_1$–$C_6$alkyl moiety is straight or branched; $R_3$ is H or $C_1$–$C_6$alkyl wherein the $C_1$–$C_6$alkyl moiety is straight or branched; and X is Cl, Br or I.

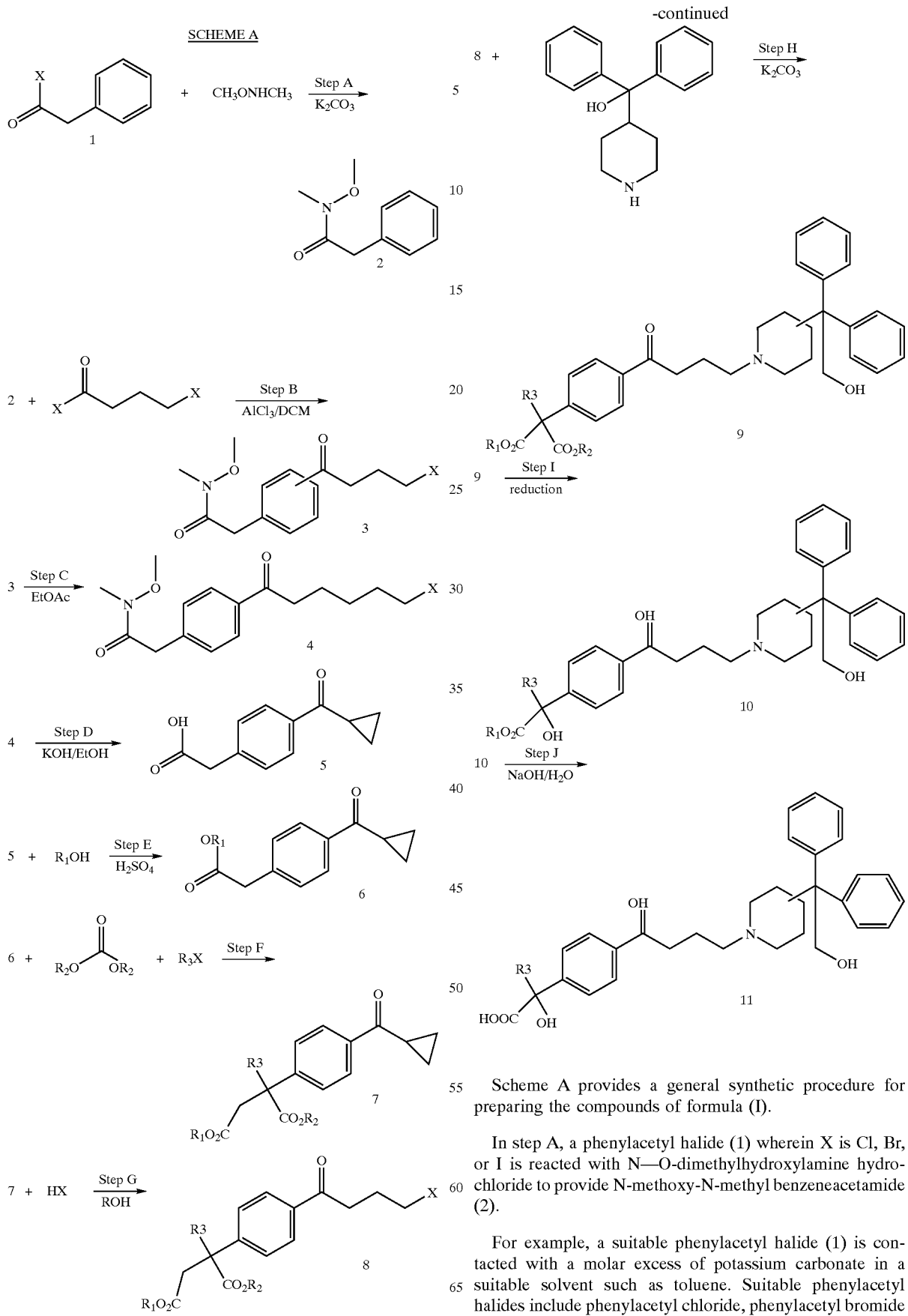

Scheme A provides a general synthetic procedure for preparing the compounds of formula (I).

In step A, a phenylacetyl halide (1) wherein X is Cl, Br, or I is reacted with N—O-dimethylhydroxylamine hydrochloride to provide N-methoxy-N-methyl benzeneacetamide (2).

For example, a suitable phenylacetyl halide (1) is contacted with a molar excess of potassium carbonate in a suitable solvent such as toluene. Suitable phenylacetyl halides include phenylacetyl chloride, phenylacetyl bromide or phenylacetyl iodide. A preferred phenylacetyl halide is phenylacetyl chloride. A molar equivalent of N—O-dimethylhydroxylamine hydrochloride dissolved in water is then added. The reaction mixture is stirred for a period of time ranging from 1 to 24 hours at a temperature range of from 0° C. to 60° C. A preferred stirring time is 3 hours. A preferred temperature is 25° C. N-methoxy-N-methyl-benzeneacetamide is (2) is recovered from the reaction zone by extractive methods as are known in the art.

In step B, N-methoxy-N-methyl-benzeneacetamide (2) is acylated with a suitable 4-halo-substituted butyrylhalide of the formula

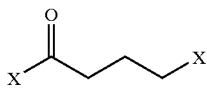

wherein each X is independently Cl, Br or I; under Friedel-Crafts conditions to give a mixture of para, meta substituted ω-halo-α-keto-benzeneacetamide (3). Surprisingly, the para isomer is readily isolated by subsequent crystallization as set forth in step C.

For example, in step B, N-methoxy-N-methylbenzeneacetamide (2) is contacted with suitable 4-halo-substituted butyrylhalide under the general conditions of a Friedel-Crafts acylation using a suitable Lewis acid. Examples of suitable 4-halo-substituted butyrylhalides include 4-chlorobutyrylchloride, 4-bromobutyrylbromide, and the like. A preferred 4-halo-substituted butyrylhalide is 4 chlorobutyrylchloride. The reaction is carried out in a solvent, such as carbon disulfide, 1,2-dichloroethane, n-hexane, acetonitrile, 1-nitropropane, nitromethane, diethyl ether, carbon tetrachloride, methylene chloride, tetrachloroethane or nitrobenzene with dichloromethane being the preferred solvent. The reaction time varies from about ½ hour to 25 hours at a temperature range of from 0° C. to 40° C. A preferred stirring time is 6 hours. A preferred temperature is 40° C. The mixture of para, meta substituted ω-halo-α-keto-benzeneacetamide (3) is recovered from the reaction zone by an aqueous quench followed by extractive methods as are known in the art.

Suitable Lewis acids for the acylation reaction described in step B are well known and appreciated in the art. Examples of suitable Lewis acids are boron trichloride, aluminum chloride, titanium tetrachloride, boron trifluoride, tin tetrachloride and zinc chloride. The selection and utilization of suitable Lewis acids for the acylation reaction of step B is well known and appreciated by one of ordinary skill in the art.

The para-substituted ω-halo-α-keto-benzeneacetamide (3) is purified by recrystallization techniques as set forth in step C.

For example, the product of the extractive methods as set forth in step B is stirred in a suitable organic solvent such as a mixture of heptane/ethyl acetate (ca. 4:1) and collected. The solid is dissolved in a suitable solvent such as ethyl acetate at a temperature range of from 25° C. to 76° C. A preferred temperature is 76° C. The solution is then contacted with charcoal. This mixture is then filtered and diluted with a suitable solvent such as heptane. The resultant slurry is then heated until a homogenous solution is obtained. Substantially pure para-substituted ω-halo-α-keto-benzeneacetamide (4) crystallizes upon standing at room temperature.

In step D, the substantially pure para-substituted ω-halo-α-keto-benzeneacetamide (4) is hydrolyzed to give the 4-(cyclopropylcarbonyl)benzeneacetic acid (5).

For example, the substantially pure para-substituted ω-halo-α-keto-benzeneacetamide (4) is contacted with a molar excess of an appropriate base such as potassium hydroxide in a suitable solvent such as ethanol. The reactants are typically stirred together for a period of time ranging from 1 to 24 hours at a temperature range of from 0° C. to 78° C. A preferred stirring time is 18 hours. A preferred temperature is 25° C. The 4-(cyclopropylcarbonyl) benzeneacetic acid (5) is recovered from the reaction zone by acidification and extractive methods as are known in the art.

In step E, the 4-(cyclopropylcarbonyl)benzeneacetic acid (5) is esterified to give the corresponding 4-(cyclopropylcarbonyl)benzeneacetic acid ester (6).

For example, the appropriate 4-(cyclopropylcarbonyl) benzeneacetic acid (5) is reacted with an excess of an appropriate $C_1$–$C_6$ alcohol which is straight or branched in the presence of a catalytic amount of mineral acid, such as hydrochloric acid or sulfuric acid, hydrochloric acid being preferred, at a temperature range of from 25° C. to 78° C. The reactants are typically stirred together for a period of time ranging from 2 to 72 hours. A preferred stirring time is 24 hours. A preferred temperature is 25° C. The corresponding 4-(cyclopropylcarbonyl)benzeneacetic acid ester (6) is recovered from the reaction zone by basification and extractive methods as are known in the art. It can be purified by silica gel chromatography.

In step F, the appropriate 4-(cyclopropylcarbonyl) benzeneacetic acid ester (6) is acylated with the appropriate acylating agent to give the corresponding [4 (cyclopropylcarbonyl)phenyl]propanedioic acid diester (7).

For example, the appropriate 4-(cyclopropylcarbonyl) benzeneacetic acid ester (6) is reacted with a slight molar excess of a suitable acylating agent. Suitable acylating agents include dialkylcarbonates, such as, dimethylcarbonate or diethylcarbonate; or chloroformates, such as, methyl chloroformate or ethyl chloroformate. The reaction is typically conducted in a suitable aprotic solvent in the presence of a suitable non-nucleophilic base from about 0.5 hour to 7 days and at a temperature of about 0° C. to the reflux temperature of the solvent. A preferred stirring time is 3 days. A preferred temperature is 25 20 C. Suitable solvents for the acylation reaction include tetrahydrofuran, dioxane, or tert-butyl methyl ether. A preferred solvent is tetrahydrofuran. Suitable non-nucleophilic bases for the acylation reaction include inorganic bases, for example, sodium bicarbonate, potassium bicarbonate, or hydrides, for example, sodium hydride or potassium hydride or alkoxides, for example, potassium tert-butoxide. A preferred base is sodium bis(trimethylsilyl)amide.

The derivative formed upon acylation is optionally alkylated with a suitable alkylating agent in situ subsequent to the acylation. Suitable alkylating agents include alkyl halides, such as, iodomethane, chloromethane or bromomethane; or dialkylsulfates, such as, dimethylsulfate or diethylsulfate. The reactants are typically stirred together for a period of time ranging from 1 to 48 hours at a temperature range of from 0° C. to 30° C. A preferred stirring time is 24 hours. A preferred temperature is 25° C.

The corresponding [4-(cyclopropylcarbonyl)phenyl] propanedioic acid diester (7) is recovered from the reaction zone by extractive methods as are known in the art. It can be purified by silica gel chromatography and/or recrystallization.

While not necessary for utilization in the acylation and subsequent alkylation in step F, the keto functionality of the 4-(cyclopropylcarbonyl)benzeneacetic acid ester (6) may be protected with a suitable protecting group. The selection and utilization of suitable protecting groups for the keto group of structure (6) is well known by one of ordinary skill in the art and is described in "Protective Groups in Organic Synthesis", Theodora W. Greene, Wiley (1981). For example, suitable protecting groups for the keto functionality include acyclic ketals such as dimethyl ketal; cyclic ketals such as 1,3-dioxanes and 1,3-dioxalanes; acyclic dithioketals such as S,S-dimethyl ketal; cyclic dithio ketals such as 1,3-dithiane and 1,3-dithiolane derivatives; acyclic monothio ketals; cyclic monothio ketals such as 1,3-oxathiolanes.

In step G, the appropriate [4-(cyclopropylcarbonyl)phenyl]propanedioic acid diester (7) is ring-opened to give the corresponding [4-(4-halo-1-oxo-butyl)phenyl]propanedioic acid diester (8).

For example, the appropriate [4-(cyclopropylcarbonyl)phenyl]propanedioic acid diester (7) is contacted with a suitable hydrogen halide such as hydrogen chloride, hydrogen bromide, or hydrogen iodide in a suitable organic solvent or in the absence of solvent. Suitable organic solvents include alcohol solvents, such as, ethanol, methanol, isopropyl alcohol, or n-butanol; hydrocarbon solvents, such as, benzene, toluene or xylene; halogenated hydrocarbons, such as chlorobenzene, chloroform or methylene chloride or dimethylformamide or acetic acid or dioxane at a temperature range of from 0° C. to 100° C. The absence of solvent is preferred. The reactants are typically stirred together for a period of time ranging from 1 hour to 24 hours. A preferred stirring time is 4 hours to 16 hours. A preferred temperature range is 60° C. to 80° C. If solvent is present, the [4-(4-halo-1-oxo-butyl)phenyl]propanedioic acid diester (8) is recovered from the reaction zone by extractive methods as are known in the art and subsequent evaporation of the solvent.

In step H, the halo functionality of the appropriate [4-(4-halo-1-oxo-butyl)phenyl]propanedioic acid diester (8) is alkylated with α-(4-pyridyl)benzhydrol (commercially available from Aldrich Chemicals) to give the corresponding [4-[4-[4-(hydroxydiphenylmethyl)-1-piperidinyl]1-oxobutyl]phenyl]propanedioic acid diester (9).

For example, the alkylation reaction is carried out in a suitable solvent preferably in the presence of a non-nucleophilic base and optionally in the presence of a catalytic amount of an iodide source, such as potassium or sodium iodide. The reaction time varies from about 4 hours to 7 days and the reaction varies from about 25° C. to the reflux temperature of the solvent. A preferred stirring time is 3 days. A preferred temperature is the reflux temperature of the solvent. Suitable solvent for the alkylation reaction include alcohol solvents such as, methanol, ethanol, isopropyl alcohol, or n-butanol; ketone solvents, such as, methyl isobutyl ketone; hydrocarbon solvents, such as, benzene, toluene or xylene, and mixtures thereof with water; halogenated hydrocarbons, such as, chlorobenzene or methylene chloride or dimethylformamide. A preferred solvent is toluene/water (10:4). Suitable non-nucleophilic bases for the alkylation reaction include inorganic bases, for example, sodium bicarbonate, potassium bicarbonate, or potassium carbonate or organic bases, such as, a trialkylamine, for example, triethylamine, or pyridine, or an excess of α-(4-pyridyl)benzhydrol may be used. A preferred base is potassium carbonate.

The corresponding [4-[4-[4-(hydroxydiphenylmethyl)-1-piperidinyl]-1-oxobutyl]phenyl]propanedioic acid diester (9) is recovered from the reaction zone by extractive methods as are known in the art. It can be purified by silica gel chromatography.

While not necessary for the utilization in the alkylation of step H, the keto functionality of the [(4-halo-1-oxo-butyl)phenyl]propanedioic acid diester (8) may be protected with a suitable protecting group. The selection and utilization of suitable protecting groups for the keto group of structure (8) is well known by one of ordinary skill in the art and is described in "Protective Groups in Organic Synthesis", Theodora W. Greene, Wiley (1981). For example, suitable protecting groups for the keto functionality include acyclic ketals such as dimethyl ketal; cyclic ketals such as 1,3-dioxanes and 1,3-dioxalanes; acyclic dithioketals such as S,S-dimethyl ketal; cyclic dithio ketals such as 1,3-dithiane and 1,3-dithiolane derivatives; acyclic monothio ketals; cyclic monothio ketals such as 1,3-oxathiolanes.

In step I, the appropriate [4-[4-[4-(hydroxydiphenylmethyl)-1-piperidinyl]-1-oxobutyl]phenyl]propanedioic acid diester (9) is reduced selectively to the corresponding 4-[1-hydroxy-4-[4-(hydroxydiphenylmethyl)-1-piperidinyl]butyl]-α-(hydroxymethyl)-benzeneacetic acid ester (10). This is accomplished by utilizing a suitable selective reducing agent. A suitable selective reducing agent is a reagent or combination of reagents which will selectively reduce only one ester of the propanedioic acid diester functionality to the corresponding hydroxymethyl moiety while not reducing the second ester of the propanedioic acid diester functionality. Suitable selective reducing agents include lithium tri-tert-butoxyaluminohydride or the combination of a suitable silane and a suitable titanocene-based catalyst.

For example, the appropriate [4-[4-[4-(hydroxydiphenylmethyl)-1-piperidinyl]-1-oxobutyl]phenyl]propanedioic acid diester (9) is contacted with a suitable selective reducing agent such as lithium tri-tert-butoxyaluminohydride in a suitable solvent such as tetrahydrofuran, diethyl ether, or dioxane. A preferred solvent is tetrahydrofuran. The reactants are typically stirred together for a period of time ranging from 0.5 hours to 168 hours at a temperature range of from 0° C. to 65° C. A preferred stirring time is 48 hours. A preferred temperature is 25° C.

Catalytic reduction may also be employed in the preparation of 4-[1-hydroxy-4-[4-(hydroxydiphenylmethyl)-1-piperidinyl]butyl]-α-(hydroxymethyl)-benzeneacetic acid ester (10) from an appropriate [4-[4-[4-(hydroxydiphenylmethyl)-1-piperidinyl]-1-oxobutyl]phenyl]propanedioic acid diester (9), using, for example, a suitable titanocene-based catalyst in which a suitable silane, such as, polymethylhydrosiloxane, serves as the stoichiometric reductant. Suitable titanocene-based catalysts include the active catalytic species commonly known as "$Cp_2TiH$". It is well known by one of ordinary skill in the art that the active catalytic species "$Cp_2TiH$" may be generated, for example, by the addition of 2 equivalents of ethyl magnesium bromide to 1 equivalent of $Cp_2TiCl_2$ in a suitable solvent such as tetrahydrofuran.

For example, the catalytic reduction is carried out in a suitable solvent such as tetrahydrofuran or diethyl ether or dioxane at temperatures ranging from about 25° C. to the reflux temperature of the solvent. A preferred temperature for use with the catalytic reduction is 65° C. The reaction time varies from about 8 hours to 24 hours. A preferred stirring time is 18 hours. The 4-[1-hydroxy-4-[4-(hydroxydiphenylmethyl)-1-piperidinyl]butyl]-α-(hydroxymethyl)-benzeneacetic acid ester (10) is recovered from the reaction zone after work-up with $Bu_4NF$ and utilization of extractive methods as are known in the art. It can be purified by silica gel chromatography.

In addition, a chiral catalytic reduction may also be employed in the preparation of enantiomerically pure 4-[1- hydroxy-4-[4-(hydroxydiphenylmethyl)-1-piperidinyl]butyl]-α-(hydroxymethyl)-benzeneacetic acid ester (10) from an appropriate [4-[4-[4-(hydroxydiphenylmethyl)-1-piperidinyl]-1-oxobutyl]phenyl]propanedioic acid diester (9), using an appropriate chiral titanocene system, such as, for example, is described in Journal of the American Chemical Society, 116, 11667–11670 (1994).

As one skilled in the art would appreciate, the [4-[4-[4-(hydroxydiphenylmethyl)-1-piperidinyl]-1-oxobutyl]phenyl]propanedioic acid diester (9) wherein the keto group is protected must be reacted with an appropriate deprotecting reagent prior to the reduction reaction described in step I. The selection and utilization of appropriate deprotecting reagents is well known by one of ordinary skill in the art and is described in "Protective Groups in Organic Synthesis", Theodora W. Greene, Wiley (1981). For example, cleavage of a dimethylketal protecting group on the keto functionality of the [4-[4-[4-(hydroxydiphenylmethyl)-1-piperidinyl]-1-oxobutyl]phenyl]propanedioic acid diester (9) can be achieved by using iodotrimethylsilane or dilute acid as is known in the art.

In step J, the appropriate 4-[1-hydroxy-4-[4-(hydroxydiphenylmethyl)-1-piperidinyl]butyl]-α-(hydroxymethyl)-benzeneacetic acid ester (10) is optionally hydrolyzed to the corresponding 4-[1-hydroxy-4-[4-(hydroxydiphenylmethyl)-1-piperidinyl]butyl]-α-(hydroxymethyl)-benzeneacetic acid (11).

For example, hydrolysis may be achieved using methods known in the art such as potassium carbonate in methanol, methanolic ammonia, potassium carbonate, potassium hydroxide, calcium hydroxide, sodium hydroxide, magnesium hydroxide, sodium hydroxide/pyridine in methanol, potassium cyanide in ethanol and sodium hydroxide in aqueous alcohols, with sodium hydroxide being preferred. The reaction is typically carried out in an aqueous lower alcohol solvent, such as methanol, ethanol, isopropyl alcohol, n-butanol, 2-ethoxyethanol or ethylene glycol or pyridine. A preferred solvent is a mixture of tetrahydrofuran/methanol/water (3:2:1). The reaction is typically carried out at temperatures ranging from room temperature to the reflux temperature of the solvent. A preferred temperature is 65° C. The reactants are typically stirred together for a period of time ranging from 1 to 24 hours. A preferred stirring time is 4 hours. The 4-[1-hydroxy-4-[4-(hydroxydiphenylmethyl)-1-piperidinyl]butyl]-α-(hydroxymethyl)-benzeneacetic acid (11) is recovered from the reaction zone by acidification and extractive methods as are known in the art.

Of course it is understood that the compound of formula (I) may exist in a variety of stereoisomers. The compound has more than one chiral center. For example, the benzylic carbon to which the carboxyl, hydroxymethyl and methyl groups attach may exist in the (R) or the (S) form. In addition, the benzylic carbon to which the hydroxy, hydrogen and alkyl amino groups attach may exist in the (R) or the (S) form. It is further understood that the present invention encompasses those compounds of formula (I) in each of their various structural and stereo isomeric configurations as individual isomers and as mixtures of isomers.

An alternative novel process for the preparation of 4-(cyclopropylcarbonyl)benzeneacetic acid is set forth in Scheme B. This compound is useful for the synthesis of compounds of formula (I) as well as fexofenadine and related compounds. In Scheme B, $R_1$ is $C_1$–$C_6$alkyl and the $C_1$–$C_6$alkyl moiety is straight or branched.

SCHEME B

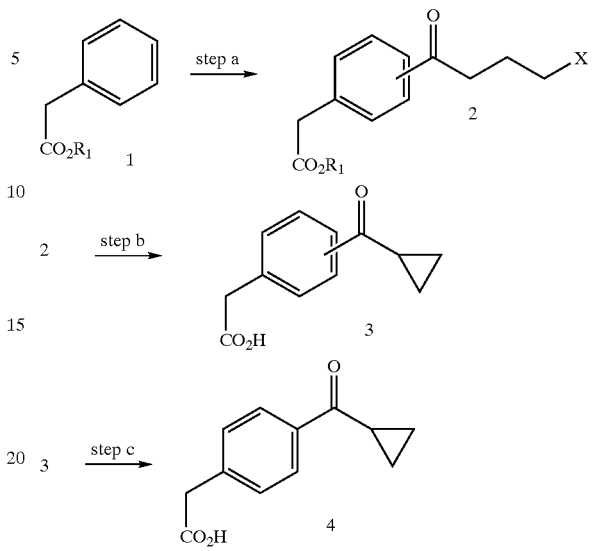

In step a of Scheme B, the appropriate benzeneacetic acid ester (1) wherein $R_1$ is $C_1$–$C_6$alkyl and the $C_1$–$C_6$alkyl moiety is straight or branched, is acylated with a suitable 4-halo-substituted butyrylhalide of the formula

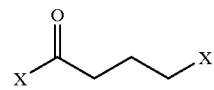

wherein each X is independently Cl, Br, or I, under Friedel-Crafts conditions to give a mixture of the corresponding para, meta substituted ω-halo-α-keto-benzeneacetic acid ester (2) wherein X is Cl, Br, or I.

For example, in step a, the appropriate benzeneacetic acid ester (1) is contacted with a 4-halo-substituted butyrylhalide under the general conditions of a Friedel-Crafts acylation using a suitable Lewis acid. Examples of suitable 4-halo-substituted butyrylhalides include 4-chlorobutyrylchloride, 4-bromobutyrylbromide, and the like. A preferred 4-halo-substituted butyrylhalide is 4-chlorobutyrylchloride. The reaction is carried out in a solvent, such as carbon disulfide, 1,2-dichloroethane, n-hexane, acetonitrile, 1-nitropropane, nitromethane, diethyl ether, carbon tetrachloride, methylene chloride, tetrachloroethane or nitrobenzene with dichloromethane being the preferred solvent. The reaction time varies from about ½ hour to 25 hours at a temperature range of from 0° C. to 40° C. A preferred stirring time is 6 hours. A preferred temperature is 40° C. The mixture of para, meta substituted ω-halo-α-keto-benzeneacetic acid ester (2) is recovered from the reaction zone by an aqueous quench followed by extractive methods as are known in the art.

Suitable Lewis acids for the acylation reaction described in step a are well known and appreciated in the art. Examples of suitable Lewis acids are boron trichloride, aluminum chloride, titanium tetrachloride, boron trifluoride, tin tetrachloride and zinc chloride. The selection and utilization of suitable Lewis acids for the acylation reaction of step a is well known and appreciated by one of ordinary skill in the art.

In step b of Scheme B, the mixture of meta- and para-substituted ω-halo-α-keto-benzeneacetic acid ester (2) is hydrolyzed to give a mixture of meta- and para-substituted (cyclopropylcarbonyl)benzeneacetic acid (3).

For example, the mixture of meta- and para-substituted ω-halo-α-keto-benzeneacetic acid (2) is contacted with a molar excess of an appropriate base such as lithium hydroxide or potassium hydroxide in a suitable solvent such as ethanol. The reactants are typically stirred together for a period of time ranging from 1 to 24 hours at a temperature range of from 0° C. to 78° C. A preferred stirring time is 18 hours. A preferred temperature is 25° C. The meta- and para-substituted (cyclopropylcarbonyl)benzeneacetic acid (3) is recovered from the reaction zone by acidification and extractive methods as are known in the art.

Surprisingly, the substantially pure para isomer is readily isolated by subsequent crystallization as set forth in step c of Scheme B.

For example, the product of the extractive methods as set forth in step b is dissolved in a suitable organic solvent such as a mixture of heptane/ethyl acetate (ca. 4:1) with heating to reflux. The solution is treated with charcoal and filtered. Upon cooling, the resultant solid is collected and recrystallized from a suitable organic solvent such as ethyl acetate/heptane. Substantially pure para-substituted (cyclopropylcarbonyl)benzeneacetic acid (4) crystallizes upon standing at room temperature.

As shown previously herein, 4-(cyclopropylcarbonyl) benzeneacetic acid has utility as an intermediate in the synthesis of compounds of formula (I). 4-(Cyclopropylcarbonyl)benzeneacetic acid may also be used as an intermediate in the process of preparing compounds of formula (7) as shown in Scheme C. Compounds of formula (7) include fexofenadine and related compounds.

SCHEME C

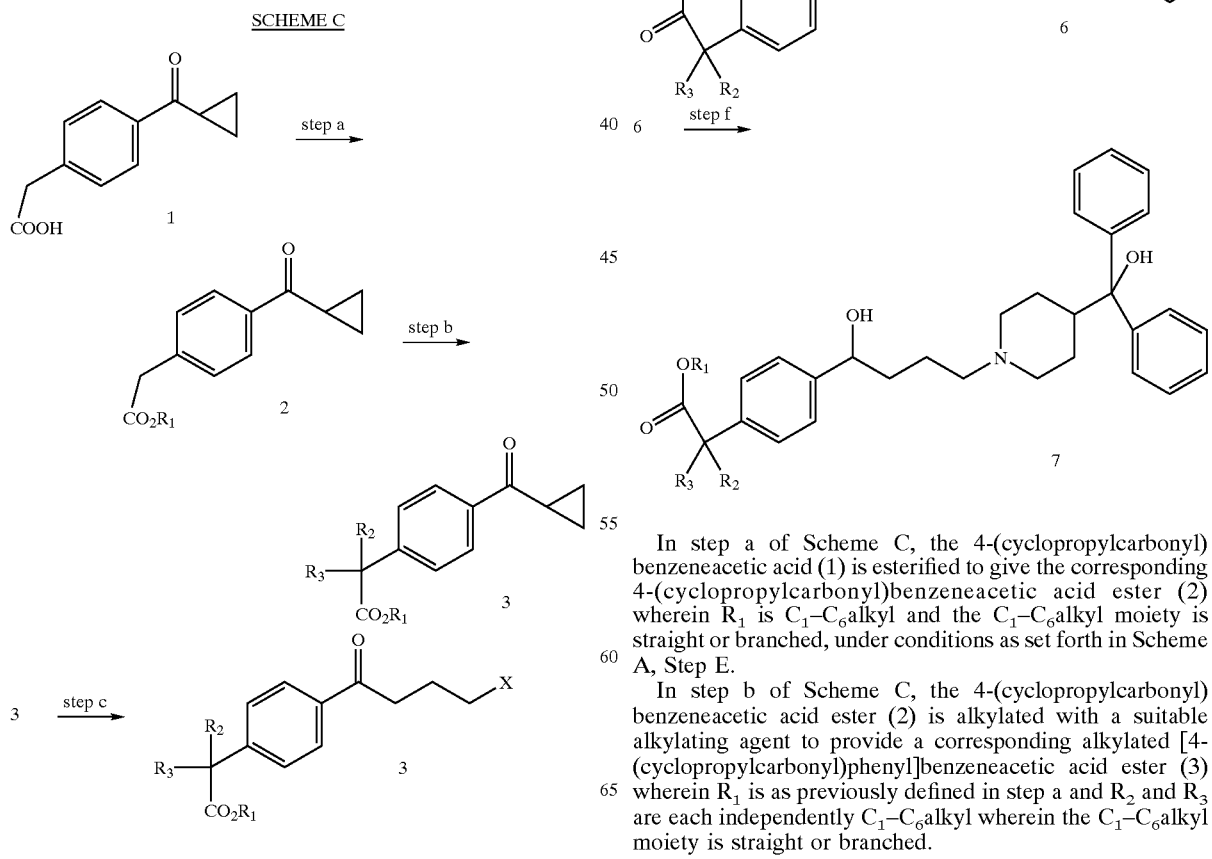

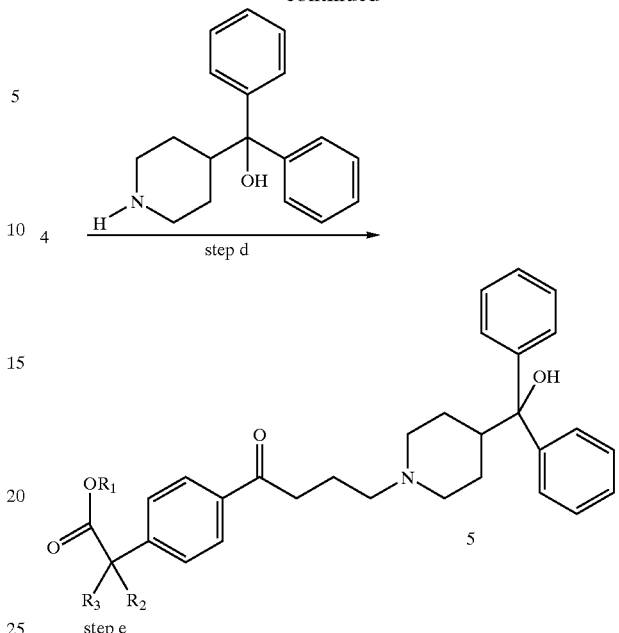

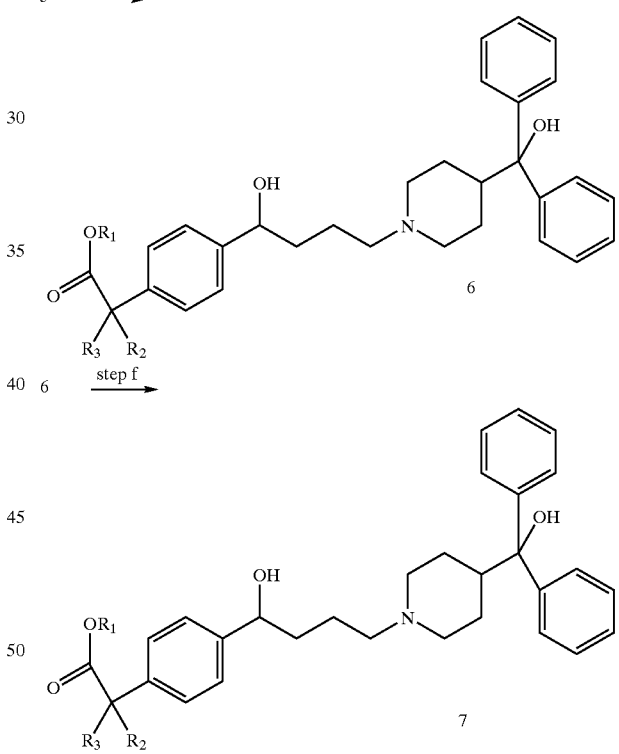

In step a of Scheme C, the 4-(cyclopropylcarbonyl)benzeneacetic acid (1) is esterified to give the corresponding 4-(cyclopropylcarbonyl)benzeneacetic acid ester (2) wherein $R_1$ is $C_1$–$C_6$alkyl and the $C_1$–$C_6$alkyl moiety is straight or branched, under conditions as set forth in Scheme A, Step E.

In step b of Scheme C, the 4-(cyclopropylcarbonyl)benzeneacetic acid ester (2) is alkylated with a suitable alkylating agent to provide a corresponding alkylated [4-(cyclopropylcarbonyl)phenyl]benzeneacetic acid ester (3) wherein $R_1$ is as previously defined in step a and $R_2$ and $R_3$ are each independently $C_1$–$C_6$alkyl wherein the $C_1$–$C_6$alkyl moiety is straight or branched.

For example, the reaction is typically conducted in a suitable aprotic solvent in the presence of a suitable non-nucleophilic base. Suitable solvents for the alkylation reaction include diglyme, tetrahydrofuran, dioxane, or tert-butyl methyl ether. A preferred solvent is diglyme. Suitable non-nucleophilic bases for the alkylation reaction include sodium bis(trimethylsilyl)amide, inorganic bases, for example, sodium bicarbonate, potassium bicarbonate, or hydrides, for example, sodium hydride or potassium hydride or alkoxides, for example, potassium tert-butoxide. A preferred base is potassium tert-butoxide. Suitable alkylating agents include alkyl halides, such as, iodomethane, chloromethane or bromomethane; or dialkylsulfates, such as, dimethylsulfate, or diethylsulfate. The reactants are typically stirred together for a period of time ranging from 1 to 48 hours at a temperature range of from 0° C. to 80° C.

In step c of Scheme C, the appropriate alkylated [4-(cyclopropylcarbonyl)phenyl]benzeneacetic acid ester (3) is ring opened to provide the corresponding [4-(4-halo-1-oxobutyl)phenyl]benzene acetic acid ester (4) wherein $R_1$, $R_2$ and $R_3$ are as previously defined in step b and X is Cl, Br or I. The reaction occurs under conditions set forth in step G of Scheme A.

In step d, the appropriate [4-(4-halo-1-oxo-butyl)phenyl] benzene acetic acid ester (4) is alkylated with α-(4-pyridyl) benzhydrol to produce a [4-[4-[4-(hydroxydiphenylmethyl)-1-piperidinyl]-1-oxobutyl]phenyl]benzeneacetic acid ester (5) wherein $R_1$, $R_2$ and $R_3$ are as previously defined in step b, under conditions that were previously disclosed in U.S. Patent No. 4,254,129, the disclosure of which is herein incorporated by reference.

In step e of Scheme C, the appropriate [4-[4-[4-(hydroxydiphenylmethyl)-1-piperidinyl]-1-oxobutyl]phenyl]benzeneacetic acid ester (5) is reacted with a suitable reducing agent to produce a 4-[1-hydroxy-4-[4-(hydroxydiphenylmethyl)-1-piperidinyl]butyl] benzeneacetic acid ester (6) wherein $R_1$, $R_2$ and $R_3$ are as previously defined in step b, under conditions that were previously disclosed in U.S. Pat. No. 4,254,129. Suitable reducing agents include, for example, sodium borohydride or potassium borohydride. Catalytic reduction using, for example, Raney nickel, palladium, platinum, or rhodium catalysts, may also be employed in step e of Scheme C.

In step f of Scheme C, the 4-[1-hydroxy-4-[4-(hydroxydiphenylmethyl)-1-piperidinyl]butyl] benzeneacetic acid ester (6) is optionally hydrolyzed to produce the 4-[1-hydroxy-4-[4-(hydroxydiphenylmethyl)-1-piperidinyl]butyl]benzeneacetic acid (7) wherein $R_2$ and $R_3$ are as previously defined in step b, under conditions that were previously disclosed in U.S. Pat. No. 4,254,129.

While not necessary for utilization in alkylation steps b and d, the keto functionality of the 4-(cyclopropylcarbonyl) benzeneacetic acid ester (6) may be protected with a suitable protecting group. The selection and utilization of suitable protecting groups for the keto group of structure (6) is well known by one of ordinary skill in the art and is described in "Protective Groups in Organic Synthesis", Theodora W. Greene, Wiley (1981). For example, suitable protecting groups for the keto functionality include acyclic ketals such as dimethyl ketal; cyclic ketals such as 1,3-dioxanes and 1,3-dioxalanes; acyclic dithioketals such as S,S-dimethyl ketal; cyclic dithio ketals such as 1,3-dithiane and 1,3-dithiolane derivatives; acyclic monothio ketals; cyclic monothio ketals such as 1,3-oxathiolanes.

The following examples present typical syntheses as described in Schemes A B and C. Starting materials for use in Schemes A, B and C are readily available to one of ordinary skill in the art. These examples are understood to be illustrative only and are not intended to limit the scope of the present invention in any way. As used herein (throughout the specification), the following terms have the indicated meanings: "g" refers to grams; "mmol" refers to millimoles; "mL refers to milliliters; "bp" refers to boiling point; "mp" refers to melting point; "C°" refers to degrees Celsius; "mm Hg" refers to millimeters of mercury; "μL" refers to microliters; "μg" refers to micrograms; and "μM" refers to micromolar.

Examples of Synthesis Set Forth in Scheme A

Step A: Preparation of N-Methoxy-N-methyl-benzeneacetamide

Dissolve potassium carbonate (100 g, 720 mmol) in water (100 mL). Add a solution of phenylacetyl chloride (50 g, 320 mmol) in toluene (250 mL). Then add a solution of N—O-dimethylhydroxylamine hydrochloride (32 g, 330 mmol) in water (100 mL) dropwise over one hour. After three hours, carefully add 10% hydrochloric acid (250 mL) and tert-butyl methyl ether (125 mL). Separate the organic phase, wash with 10% hydrochloric acid and saturated sodium hydrogen carbonate solution. Dry over anhydrous magnesium sulfate and concentrate to give the title compound (55 g, 95%).

Step B: Preparation of [4-(4-Chloro-1-oxobutyl)]-N-methoxy-N-methyl benzeneacetamide Cool a slurry of aluminum chloride (87 g, 650 mmol) in methylene chloride (100 mL) with an ice bath. Add 4-chlorobutyryl chloride (51 g, 360 mL) dropwise over 0.5 hours. Add N-methoxy-N-methyl-benzeneacetamide (53 g; 300 mmol) over 0.5 hours. Allow the resultant solution to warm to room temperature. Then heat at reflux for 6 hours. Cool the solution to room temperature. Pour the solution into ice (1 L) and add methylene chloride (1 L). Separate the organic phase. Extract the aqueous phase with methylene chloride (2×500 mL). Dry the combined organics over anhydrous magnesium sulfate and concentrate to provide a solid which contains a ca. 1:1 mixture of the title compound and the meta isomer.

Step C: Crystallization of [4-(4-Chloro-1-oxobutyl)]-N-methoxy-N-methyl-benzeneacetamide Slurry the solid obtained in step B in heptane/ethyl acetate (ca. 4:1) and then collect it. Dissolve the solid in hot ethyl acetate and treat the resultant solution with ca. 5 g of charcoal. Filter through diatomaceous earth and add heptane (60 mL). Heat the slurry until a homogenous solution is obtained. Allow the solution to stand overnight at room temperature. Filter the resultant crystalline solid and wash with heptane to provide purified [4-(4-chloro-1-oxobutyl)]-N-methoxy-N-methyl-benzeneacetamide (20 g). Allow the mother liquor to stand for 5 days and collect a second crop of the crystalline solid (3.0 g) to obtain a total of 23 g (28%) of the purified [4-(4-chloro-1-oxobutyl)]-N-methoxy-N-methyl-benzeneacetamide.

Step D: Preparation of 4-(Cyclopropylcarbonyl) benzeneacetic acid

Add purified [4-(4-chloro-1-oxobutyl)]-N-methoxy-N-methyl-benzeneacetamide (9.4 g, 330 mmol) to a solution of potassium hydroxide (22.0 g) in ethanol (160 mL). Stir 18 hours. Pour the solution into dilute hydrochloric acid (30 mL of concentrated hydrochloric acid in 500 mL of water). Extract the solution with three 500-mL portions of ethyl acetate. Dry the combined organic phases over anhydrous magnesium sulfate and concentrate to give the title compound (6.4 g, 95%).

Step E: Preparation of 4-(cyclopropylcarbonyl) benzeneacetic acid ethyl ester

Dissolve 4-(cyclopropylcarbonyl)benzeneacetic acid in ethanol (150 mL) containing concentrated sulfuric acid (10 drops). Stir 24 hours. Add triethylamine (2 mL) and concentrate the solution. Dissolve the residue in water/ethyl acetate. Wash the organic phase with saturated sodium hydrogen carbonate solution, dry over anhydrous magnesium sulfate and concentrate. Purify by silica gel chromatography (400 mL silica gel, 20% ethyl acetate/heptane as eluent) to give the title compound (7.0 g, 88%).

Step E: Preparation of 4-(cyclopropylcarbonyl) benzeneacetic acid, methyl ester

Dissolve 4-(cyclopropylcarbonyl)benzeneacetic acid in methanol (100 mL) containing concentrated sulfuric acid (10 drops). Stir 24 hours. Add triethylamine (2 mL) and concentrate the solution. Dissolve the residue in water/ethyl acetate. Wash the organic phase with saturated sodium hydrogen carbonate solution, dry over anhydrous magnesium sulfate and concentrate. Purify by silica gel chromatography (400 mL silica gel, 20% ethyl acetate/heptane as eluent) to give the title compound (4.6 g, 68%).

Step F: Preparation of [4-(cyclopropylcarbonyl)phenyl] methyl-propanedioic acid, diethyl ester Dissolve 4-(cyclopropylcarbonyl)benzeneacetic acid, ethyl ester (6.5 g, 28 mmol) and diethylcarbonate (4.0 g, 34 mmol) in tetrahydrofuran (100 mL). Add 62 mL (62 mmol) of a 1.0 molar solution of sodium bis(trimethylsilyl)amide in tetrahydrofuran over 0.5 hours. Stir 28 hours. Add iodomethane (5.3 g, 35 mmol). Stir 2 days. Add water and ethyl acetate. Wash organic phase with brine, dry over anhydrous magnesium sulfate and concentrate. Purify by flash chromatography (200 g silica gel, ethyl acetate/heptane as eluent) to give the title compound (1.43 g, 17%).

Step F: Preparation of [4-(cyclopropylcarbonyl)phenyl] methyl-propanedioic acid, dimethyl ester Dissolve 4-(cyclopropylcarbonyl)benzeneacetic acid, methyl ester (1.5 g, 6.0 mmol) and dimethylcarbonate (930 mg, 10.3 mmol) in tetrahydrofuran (10 mL). Add 20 mL (20 mmol) of a 1.0 molar solution of sodium bis(trimethylsilyl) amide in tetrahydrofuran over 0.5 hours. Stir 3 days. Add iodomethane (5.3 g, 35 mmol). Stir 24 hours. Add water and ethyl acetate. Wash organic phase with brine, dry over anhydrous magnesium sulfate and concentrate. Purify by flash chromatography (50 g silica gel, ethyl acetate/heptane as eluent) to give the title compound (315 mg, 16%).

Additionally, the following compounds can be prepared by the synthetic procedure depicted in Step F:

[4-(cyclopropylcarbonyl)phenyl]methyl-propanedioic acid, ethyl methyl diester
[4-(cyclopropylcarbonyl)phenyl]methyl-propanedioic acid, methyl propyl diester
[4-(cyclopropylcarbonyl)phenyl]methyl-propanedioic acid, butyl methyl diester
[4-(cyclopropylcarbonyl)phenyl]methyl-propanedioic acid, methyl pentyl diester
[4-(cyclopropylcarbonyl)phenyl]methyl-propanedioic acid, hexyl methyl diester
[4-(cyclopropylcarbonyl)phenyl]methyl-propanedioic acid, ethyl propyl diester
[4-(cyclopropylcarbonyl)phenyl]methyl-propanedioic acid, butyl ethyl diester
[4-(cyclopropylcarbonyl)phenyl]methyl-propanedioic acid, ethyl pentyl diester
[4-(cyclopropylcarbonyl)phenyl]methyl-propanedioic acid, ethyl hexyl diester
[4-(cyclopropylcarbonyl)phenyl]methyl-propanedioic acid, dipropyl ester
[4-(cyclopropylcarbonyl)phenyl]methyl-propanedioic acid, butyl propyl diester
[4-(cyclopropylcarbonyl)phenyl]methyl-propanedioic acid, pentyl propyl diester
[4-(cyclopropylcarbonyl)phenyl]methyl-propanedioic acid, hexyl propyl diester
[4-(cyclopropylcarbonyl)phenyl]methyl-propanedioic acid, dibutyl ester
[4-(cyclopropylcarbonyl)phenyl]methyl-propanedioic acid, butyl pentyl diester
[4-(cyclopropylcarbonyl)phenyl]methyl-propanedioic acid, butyl hexyl diester
[4-(cyclopropylcarbonyl)phenyl]methyl-propanedioic acid, dipentyl ester
[4-(cyclopropylcarbonyl)phenyl]methyl-propanedioic acid, hexyl pentyl diester
[4-(cyclopropylcarbonyl)phenyl]methyl-propanedioic acid, dihexyl ester
[4-(cyclopropylcarbonyl)phenyl]ethyl-propanedioic acid, diethyl ester
[4-(cyclopropylcarbonyl)phenyl]ethyl-propanedioic acid, dimethyl ester
[4-(cyclopropylcarbonyl)phenyl]ethyl-propanedioic acid, ethyl methyl diester
[4-(cyclopropylcarbonyl)phenyl]ethyl-propanedioic acid, methyl propyl diester
[4-(cyclopropylcarbonyl)phenyl]ethyl-propanedioic acid, butyl methyl diester
[4-(cyclopropylcarbonyl)phenyl]ethyl-propanedioic acid, methyl pentyl diester
[4-(cyclopropylcarbonyl)phenyl]ethyl-propanedioic acid, hexyl methyl diester
[4-(cyclopropylcarbonyl)phenyl]ethyl-propanedioic acid, ethyl propyl diester
[4-(cyclopropylcarbonyl)phenyl]ethyl-propanedioic acid, butyl ethyl diester
[4-(cyclopropylcarbonyl)phenyl]ethyl-propanedioic acid, ethyl pentyl diester
[4-(cyclopropylcarbonyl)phenyl]ethyl-propanedioic acid, ethyl hexyl diester
[4-(cyclopropylcarbonyl)phenyl]ethyl-propanedioic acid, dipropyl ester
[4-(cyclopropylcarbonyl)phenyl]ethyl-propanedioic acid, butyl propyl diester
[4-(cyclopropylcarbonyl)phenyl]ethyl-propanedioic acid, pentyl propyl diester
[4-(cyclopropylcarbonyl)phenyl]ethyl-propanedioic acid, hexyl propyl diester
[4-(cyclopropylcarbonyl)phenyl]ethyl-propanedioic acid, dibutyl ester
[4-(cyclopropylcarbonyl)phenyl]ethyl-propanedioic acid, butyl pentyl diester
[4-(cyclopropylcarbonyl)phenyl]ethyl-propanedioic acid, butyl hexyl diester
[4-(cyclopropylcarbonyl)phenyl]ethyl-propanedioic acid, dipentyl ester
[4-(cyclopropylcarbonyl)phenyl]ethyl-propanedioic acid, hexyl pentyl diester
[4-(cyclopropylcarbonyl)phenyl]ethyl-propanedioic acid, dihexyl ester
[4-(cyclopropylcarbonyl)phenyl]propyl-propanedioic acid, diethyl ester
[4-(cyclopropylcarbonyl)phenyl]propyl-propanedioic acid, dimethyl ester
[4-(cyclopropylcarbonyl)phenyl]propyl-propanedioic acid, ethyl methyl diester
[4-(cyclopropylcarbonyl)phenyl]propyl-propanedioic acid, methyl propyl diester
[4-(cyclopropylcarbonyl)phenyl]propyl-propanedioic acid, butyl methyl diester
[4-(cyclopropylcarbonyl)phenyl]propyl-propanedioic acid, methyl pentyl diester

[4-(cyclopropylcarbonyl)phenyl]propyl-propanedioic acid, hexyl methyl diester
[4-(cyclopropylcarbonyl)phenyl]propyl-propanedioic acid, ethyl propyl diester
[4-(cyclopropylcarbonyl)phenyl]propyl-propanedioic acid, butyl ethyl diester
[4-(cyclopropylcarbonyl)phenyl]propyl-propanedioic acid, ethyl pentyl diester
[4-(cyclopropylcarbonyl)phenyl]propyl-propanedioic acid, ethyl hexyl diester
[4-(cyclopropylcarbonyl)phenyl]propyl-propanedioic acid, dipropyl ester
[4-(cyclopropylcarbonyl)phenyl]propyl-propanedioic acid, butyl propyl diester
[4-(cyclopropylcarbonyl)phenyl]propyl-propanedioic acid, pentyl propyl diester
[4-(cyclopropylcarbonyl)phenyl]propyl-propanedioic acid, hexyl propyl diester
[4-(cyclopropylcarbonyl)phenyl]propyl-propanedioic acid, dibutyl ester
[4-(cyclopropylcarbonyl)phenyl]propyl-propanedioic acid, butyl pentyl diester
[4-(cyclopropylcarbonyl)phenyl]propyl-propanedioic acid, butyl hexyl diester
[4-(cyclopropylcarbonyl)phenyl]propyl-propanedioic acid, dipentyl ester
[4-(cyclopropylcarbonyl)phenyl]propyl-propanedioic acid, hexyl pentyl diester
[4-(cyclopropylcarbonyl)phenyl]propyl-propanedioic acid, dihexyl ester
[4-(cyclopropylcarbonyl)phenyl]butyl-propanedioic acid, diethyl ester
[4-(cyclopropylcarbonyl)phenyl]butyl-propanedioic acid, dimethyl ester
[4-(cyclopropylcarbonyl)phenyl]butyl-propanedioic acid, ethyl methyl diester
[4-(cyclopropylcarbonyl)phenyl]butyl-propanedioic acid, methyl propyl diester
[4-(cyclopropylcarbonyl)phenyl]butyl-propanedioic acid, butyl methyl diester
[4-(cyclopropylcarbonyl)phenyl]butyl-propanedioic acid, methyl pentyl diester
[4-(cyclopropylcarbonyl)phenyl]butyl-propanedioic acid, hexyl methyl diester
[4-(cyclopropylcarbonyl)phenyl]butyl-propanedioic acid, ethyl propyl diester
[4-(cyclopropylcarbonyl)phenyl]butyl-propanedioic acid, ethyl propyl diester
[4-(cyclopropylcarbonyl)phenyl]butyl-propanedioic acid, butyl ethyl diester
[4-(cyclopropylcarbonyl)phenyl]butyl-propanedioic acid, ethyl pentyl diester
[4-(cyclopropylcarbonyl)phenyl]butyl-propanedioic acid, ethyl hexyl diester
[4-(cyclopropylcarbonyl)phenyl]butyl-propanedioic acid, dipropyl ester
[4-(cyclopropylcarbonyl)phenyl]butyl-propanedioic acid, butyl propyl diester
[4-(cyclopropylcarbonyl)phenyl]butyl-propanedioic acid, pentyl propyl diester
[4-(cyclopropylcarbonyl)phenyl]butyl-propanedioic acid, hexyl diester
[4-(cyclopropylcarbonyl)phenyl]butyl-propanedioic acid, dibutyl ester
[4-(cyclopropylcarbonyl)phenyl]butyl-propanedioic acid, butyl pentyl diester
[4-(cyclopropylcarbonyl)phenyl]butyl-propanedioic acid, butyl hexyl diester
[4-(cyclopropylcarbonyl)phenyl]butyl-propanedioic acid, dipentyl ester
[4-(cyclopropylcarbonyl)phenyl]butyl-propanedioic acid, hexyl pentyl diester
[4-(cyclopropylcarbonyl)phenyl]butyl-propanedioic acid, dihexyl ester
[4-(cyclopropylcarbonyl)phenyl]pentyl-propanedioic acid, diethyl ester
[4-(cyclopropylcarbonyl)phenyl]pentyl-propanedioic acid, dimethyl ester
[4-(cyclopropylcarbonyl)phenyl]pentyl-propanedioic acid, ethyl methyl diester
[4-(cyclopropylcarbonyl)phenyl]pentyl-propanedioic acid, methyl propyl diester
[4-(cyclopropylcarbonyl)phenyl]pentyl-propanedioic acid, butyl methyl diester
[4-(cyclopropylcarbonyl)phenyl]pentyl-propanedioic acid, methyl pentyl diester
[4-(cyclopropylcarbonyl)phenyl]pentyl-propanedioic acid, hexyl methyl diester
[4-(cyclopropylcarbonyl)phenyl]pentyl-propanedioic acid, ethyl propyl diester
[4-(cyclopropylcarbonyl)phenyl]pentyl-propanedioic acid, butyl ethyl diester
[4-(cyclopropylcarbonyl)phenyl]pentyl-propanedioic acid, ethyl pentyl diester
[4-(cyclopropylcarbonyl)phenyl]pentyl-propanedioic acid, ethyl hexyl diester
[4-(cyclopropylcarbonyl)phenyl]pentyl-propanedioic acid, dipropyl ester
[4-(cyclopropylcarbonyl)phenyl]pentyl-propanedioic acid, butyl propyl diester
[4-(cyclopropylcarbonyl)phenyl]pentyl-propanedioic acid, pentyl propyl diester
[4-(cyclopropylcarbonyl)phenyl]pentyl-propanedioic acid, hexyl propyl diester
[4-(cyclopropylcarbonyl)phenyl]pentyl-propanedioic acid, dibutyl ester
[4-(cyclopropylcarbonyl)phenyl]pentyl-propanedioic acid, butyl pentyl diester
[4-(cyclopropylcarbonyl)phenyl]pentyl-propanedioic acid, butyl hexyl diester
[4-(cyclopropylcarbonyl)phenyl]pentyl-propanedioic acid, dipentyl ester
[4-(cyclopropylcarbonyl)phenyl]pentyl-propanedioic acid, hexyl pentyl diester
[4-(cyclopropylcarbonyl)phenyl]pentyl-propanedioic acid, dihexyl ester
[4-(cyclopropylcarbonyl)phenyl]hexyl-propanedioic acid, diethyl ester
[4-(cyclopropylcarbonyl)phenyl]hexyl-propanedioic acid, dimethyl ester
[4-(cyclopropylcarbonyl)phenyl]hexyl-propanedioic acid, ethyl methyl diester
[4-(cyclopropylcarbonyl)phenyl]hexyl-propanedioic acid, methyl propyl diester
[4-(cyclopropylcarbonyl)phenyl]hexyl-propanedioic acid, butyl methyl diester
[4-(cyclopropylcarbonyl)phenyl]hexyl-propanedioic acid, methyl pentyl diester
[4-(cyclopropylcarbonyl)phenyl]hexyl-propanedioic acid, hexyl methyl diester
[4-(cyclopropylcarbonyl)phenyl]hexyl-propanedioic acid, ethyl propyl diester
[4-(cyclopropylcarbonyl)phenyl]hexyl-propanedioic acid, butyl ethyl diester
[4-(cyclopropylcarbonyl)phenyl]hexyl-propanedioic acid, ethyl pentyl diester

[4-(cyclopropylcarbonyl)phenyl]hexyl-propanedioic acid, ethyl hexyl diester

[4-(cyclopropylcarbonyl)phenyl]hexyl-propanedioic acid, dipropyl ester

[4-(cyclopropylcarbonyl)phenyl]hexyl-propanedioic acid, butyl propyl diester

[4-(cyclopropylcarbonyl)phenyl]hexyl-propanedioic acid, pentyl propyl diester

[4-(cyclopropylcarbonyl)phenyl]hexyl-propanedioic acid, hexyl propyl diester

[4-(cyclopropylcarbonyl)phenyl]hexyl-propanedioic acid, dibutyl ester

[4-(cyclopropylcarbonyl)phenyl]hexyl-propanedioic acid, butyl pentyl diester

[4-(cyclopropylcarbonyl)phenyl]hexyl-propanedioic acid, butyl hexyl diester

[4-(cyclopropylcarbonyl)phenyl]hexyl-propanedioic acid, dipentyl ester

[4-(cyclopropylcarbonyl)phenyl]hexyl-propanedioic acid, hexyl pentyl diester

[4-(cyclopropylcarbonyl)phenyl]hexyl-propanedioic acid, dihexyl ester

Step G: Preparation of [4-(4-chloro-1-oxobutyl)phenyl]methyl-propanedioic acid, diethyl ester Bubble hydrogen chloride gas through a solution of [4-(cyclopropylcarbonyl)phenyl]methyl-propanedioic acid, diethyl ester (570 mg, 2.0 mmol) in ethanol (4 mL) for 5 minutes. Heat the solution to reflux. After 18 hours, cool the solution to room temperature and bubble nitrogen through the solution for 1 hour. Add ethyl acetate and water to the residue. Dry the organic phase over anhydrous magnesium sulfate and concentrate. Dissolve the crude product in ethanol (50 mL) and bubble hydrogen chloride gas through the solution for 10 minutes. Heat the solution to reflux. After stirring 2 days, concentrate the solution. Add water and ethyl acetate to the residue. Dry the organic phase over anhydrous magnesium sulfate and concentrate. Purify by flash chromatography (150 g silica gel, 20% ethyl acetate/heptane as eluent) to give the title compound (409 mg, 59%).

Step G: Preparation of [4-(4-chloro-1-oxobutyl)phenyl]methyl-propanedioic acid, dimethyl ester Bubble hydrogen chloride gas through a solution of [4-(cyclopropylcarbonyl)phenyl]methyl-propanedioic acid, dimethyl ester (315 mg, 1.1 mmol) in ethanol (3 mL) and toluene (9 mL) for 10 minutes. Heat the solution to 68° C. After 4 hours, cool the solution to room temperature and bubble nitrogen through the solution for 1 hour. Add ethyl acetate and water to the residue. Dry the organic phase over anhydrous magnesium sulfate and concentrate to give the title compound (321 mg, 91%).

Additionally, the following compounds can be prepared by the synthetic procedure depicted in Step G:

[4-(4-bromo-1-oxobutyl)phenyl]methyl-propanedioic acid, diethyl ester

[4-(4-iodo-1-oxobutyl)phenyl]methyl-propanedioic acid, diethyl ester

[4-(4-bromo-1-oxobutyl)phenyl]methyl-propanedioic acid, dimethyl ester

[4-(4-iodo-1-oxobutyl)phenyl]methyl-propanedioic acid, dimethyl ester

Furthermore, compounds derived from all permutations of substituents as set forth in the illustrative examples following Step F can be prepared by the synthetic procedure depicted in Step G.

Step H: Preparation of [4-[4-[4-(hydroxydiphenylmethyl)-1-piperidinyl]-1-oxobutyl]phenyl]methyl-propanedioic acid, diethyl ester Mix together [4-(4-chloro-1-oxobutyl)phenyl]methyl-propanedioic acid, diethyl ester (380 mg, 1.1 mmol), potassium carbonate (450 mg, 3.2 mmol), α-(4-pyridyl)benzhydrol (500 mg, 1.9 mmol), water (4 mL) and toluene (10 mL). Heat the mixture to reflux. After 7 days, cool to room temperature. Add ethyl acetate and water. Wash the organic phase with brine, dry over anhydrous magnesium sulfate and concentrate. Purify by flash chromatography (200 g of silica gel, 10% methanol/chloroform as eluent) to give the title compound (627 mg, 99%).

Step H: Preparation of [4-[4-[4-(hydroxydiphenylmethyl)-1-piperidinyl]1-oxobutyl]phenyl]methyl-propanedioic acid, dimethyl ester Mix together [4-(4-chloro-1-oxobutyl)phenyl]methyl-propanedioic acid, dimethyl ester (300 mg, 0.92 mmol), potassium carbonate (350 mg, 2.5 mmol), α-(4-pyridyl)benzhydrol (500 mg, 1.9 mmol), water (3 mL) and toluene (7 mL). Heat the mixture to reflux. After 5 days, cool to room temperature. Add ethyl acetate and water. Wash the organic phase with brine, dry over anhydrous magnesium sulfate and concentrate. Purify by flash chromatography (150 g of silica gel, 10% methanol/chloroform as eluent) to give the title compound (387 mg, 76%). Additionally, compounds derived from all permutations of substituents as set forth in the illustrative examples following Step F can be prepared by the synthetic procedure depicted in Step H.

Step I: Preparation of 4-[1-hydroxy-4-[4-(hydroxydiphenylmethyl)-1-piperidinyl]butyl]-α-(hydroxymethyl)-α-methyl-benzeneacetic acid, ethyl ester Dissolve [4-[4-[4-(hydroxydiphenylmethyl)-1-piperidinyl]-1-oxobutyl]phenyl]methyl-propanedioic acid, diethyl ester (515 mg, 0.88 mmol) in tetrahydrofuran (5 mL) and cool the solution with an ice bath. Add lithium tri-tert-butoxyaluminohydride (10 mL of a 1 molar solution in tetrahydrofuran, 10 mmol) portionwise over 20 minutes. After 2 hours, allow the solution to warm to room temperature. After 48 hours, cool the solution with an ice bath and add a 10% potassium hydrogen sulfate aqueous solution (10 mL). Wash the organic phase with brine, dry over anhydrous magnesium sulfate, and concentrate. Purify by flash chromatography (150 g of silica gel, 5% methanol/chloroform as eluent) to give the compound (321 mg, 67%).

Additionally, the following compounds can be prepared by the synthetic procedure depicted in Step 1:

4-[1-hydroxy-4-[4-(hydroxydiphenylmethyl)-1-piperidinyl]butyl]-α-(hydroxymethyl)-α-methyl-benzeneacetic acid, methyl ester 4-[1-hydroxy-4-[4-(hydroxydiphenylmethyl)-1-piperidinyl]butyl]-α-(hydroxymethyl)-α-methyl-benzeneacetic acid, propyl ester 4-[1-hydroxy-4-[4-(hydroxydiphenylmethyl)-1-piperidinyl]butyl]-α-(hydroxymethyl)-α-methyl-benzeneacetic acid, butyl ester 4-[1-hydroxy-4-[4-(hydroxydiphenylmethyl)-1-piperidinyl]butyl]-α-(hydroxymethyl)-α-methyl-benzeneacetic acid, pentyl ester 4-[1-hydroxy-4-[4-(hydroxydiphenylmethyl)-1-piperidinyl]butyl]-α-(hydroxymethyl)-α-methyl-benzeneacetic acid, hexyl ester 4-[1-hydroxy-4-[4-(hydroxydiphenylmethyl)-1-piperidinyl]butyl]-α-(hydroxymethyl)-α-ethyl-benzeneacetic acid, methyl ester 4-[1-hydroxy-4-[4-(hydroxydiphenylmethyl)-1-piperidinyl]butyl]-α-(hydroxymethyl)-α-ethyl-benzeneacetic acid, ethyl ester 4-[1-hydroxy-4-[4-(hydroxydiphenylmethyl)-1-piperidinyl]butyl]-α-(hydroxymethyl)-α-ethyl-benzeneacetic acid, propyl ester 4-[1-hydroxy-4-[4-(hydroxydiphenylmethyl)-1-piperidinyl]butyl]-α-(hydroxymethyl)-α-ethyl-benzeneacetic acid, butyl ester 4-[1-hydroxy-4-[4-(hydroxydiphenylmethyl)-1-piperidinyl]butyl]-α-(hydroxymethyl)-α-ethyl-benzeneacetic acid, pentyl ester 4-[1-hydroxy-4-[4-(hydroxydiphenylmethyl)-1-piperidinyl]butyl]-α-(hydroxymethyl)-α-ethyl-benzeneacetic acid, hexyl ester 4-[1-hydroxy-4-[4-(hydroxydiphenylmethyl)-1-piperidinyl]butyl]-α-(hydroxymethyl)-α-propyl-benzeneacetic acid, methyl ester 4-[1-hydroxy-4-[4-(hydroxydiphenylmethyl)-1-piperidinyl]butyl]-α-(hydroxymethyl)-α-propyl-benzeneacetic acid, ethyl ester 4-[1-hydroxy-4-[4-(hydroxydiphenylmethyl)-1-piperidinyl]butyl]-α-(hydroxymethyl)-α-propyl-benzeneacetic acid, propyl ester 4-[1-hydroxy-4-[4-(hydroxydiphenylmethyl)-1-piperidinyl]butyl]-α-(hydroxymethyl)-α-propyl-benzeneacetic acid, butyl ester 4-[1-hydroxy-4-[4-(hydroxydiphenylmethyl)-1-piperidinyl]butyl]-α-(hydroxymethyl)-α-propyl-benzeneacetic acid, pentyl ester 4-[1-hydroxy-4-[4-(hydroxydiphenylmethyl-1-piperidinyl]butyl]-α-(hydroxymethyl)-α-propyl-benzeneacetic acid, hexyl ester 4-[1-hydroxy-4-[4-(hydroxydiphenylmethyl)-1-piperidinyl]butyl]-α-(hydroxymethyl)-α-butyl-benzeneacetic acid, methyl ester 4-[1-hydroxy-4-[4-(hydroxydiphenylmethyl)-1-piperidinyl]butyl]-α-(hydroxymethyl)-α-butyl-benzeneacetic acid, ethyl ester 4-[1-hydroxy-4-[4-(hydroxydiphenylmethyl)-1-piperidinyl]butyl]-α-(hydroxymethyl)-α-butyl-benzeneacetic acid, propyl ester 4-[1-hydroxy-4-[4-(hydroxydiphenylmethyl)-1-piperidinyl]butyl]-α-(hydroxymethyl)-α-butyl-benzeneacetic acid, butyl ester 4-[1-hydroxy-4-[4-(hydroxydiphenylmethyl)-1-piperidinyl]butyl]-α-(hydroxymethyl)-α-butyl-benzeneacetic acid, pentyl ester 4-[1-hydroxy-4-[4-(hydroxydiphenylmethyl)-1-piperidinyl]butyl]-α-(hydroxymethyl)-α-butyl-benzeneacetic acid, hexyl ester 4-[1-hydroxy-4-[4-(hydroxydiphenylmethyl)-1-piperidinyl]butyl]-α-(hydroxymethyl)-α-pentyl-benzeneacetic acid, methyl ester 4-[1-hydroxy-4-[4-(hydroxydiphenylmethyl)-1-piperidinyl]butyl]-α-(hydroxymethyl)-α-pentyl-benzeneacetic acid, ethyl ester 4-[1-hydroxy-4-[4-(hydroxydiphenylmethyl)-1-piperidinyl]butyl]-α-(hydroxymethyl)-α-pentyl-benzeneacetic acid, propyl ester 4-[1-hydroxy-4-[4-(hydroxydiphenylmethyl)-1-piperidinyl]butyl]-α-(hydroxymethyl)-α-pentyl-benzeneacetic acid, butyl ester 4-[1-hydroxy-4-[4-(hydroxydiphenylmethyl)-1-piperidinyl]butyl]-α-(hydroxymethyl)-α-pentyl-benzeneacetic acid, pentyl ester 4-[1-hydroxy-4-[4-(hydroxydiphenylmethyl)-1-piperidinyl]butyl]-α-(hydroxymethyl)-α-pentyl-benzeneacetic acid, hexyl ester 4-[1-hydroxy-4-[4-(hydroxydiphenylmethyl)-1-piperidinyl]butyl]-α-(hydroxymethyl)-α-hexyl-benzeneacetic acid, methyl ester 4-[1-hydroxy-4-[4-(hydroxydiphenylmethyl)-1-piperidinyl]butyl]-α-(hydroxymethyl)-α-hexyl-benzeneacetic acid, ethyl ester 4-[1-hydroxy-4-[4-(hydroxydiphenylmethyl)-1-piperidinyl]butyl]-α-(hydroxymethyl)-α-hexyl-benzeneacetic acid, propyl ester 4-[1-hydroxy-4-[4-(hydroxydiphenylmethyl)-1-piperidinyl]butyl]-α-(hydroxymethyl)-α-hexyl-benzeneacetic acid, butyl ester 4-[1-hydroxy-4-[4-(hydroxydiphenylmethyl)-1-piperidinyl]butyl]-α-(hydroxymethyl)-α-hexyl-benzeneacetic acid, pentyl ester 4-[1-hydroxy-4-[4-(hydroxydiphenylmethyl)-1-piperidinyl]butyl]-α-(hydroxymethyl)-α-hexyl-benzeneacetic acid, hexyl ester Step J: Preparation of 4-[1-hydroxy-4-[4-(hydroxydiphenylmethyl)-1-piperidinyl]butyl]-α-(hydroxymethyl)-α-methyl-benzeneacetic acid Dissolve 4-[1-hydroxy-4-[4-(hydroxydiphenylmethyl)-1-piperidinyl]butyl]-α-(hydroxymethyl)-α-methyl-benzeneacetic acid, ethyl ester (200 mg, 0.37 mmol) in methanol (8 mL) and tetrahydrofuran (12 mL). Add 1.6 mL (1.6 mmol) of a 1 molar solution of aqueous sodium hydroxide. After 4 hours, cool the solution to room temperature and add 10% hydrochloric acid (ca. 1 mL) dropwise until pH is 5–6. Concentrate the solution and purify by flash chromatography (50 g of silica gel, methanol/chloroform gradient elution) to give the title compound (127 mg, 66%). Additionally, the following compounds can be prepared by the synthetic procedure depicted in Step J:

4-[1-hydroxy-4-[4-(hydroxydiphenylmethyl)-1-piperidinyl]butyl]-α-(hydroxymethyl)-α-ethyl-benzeneacetic acid 4-[1-hydroxy-4-[4-(hydroxydiphenylmethyl)-1-piperidinyl]butyl]-α-(hydroxymethyl)-α-propyl-benzeneacetic acid 4-[1-hydroxy-4-[4-(hydroxydiphenylmethyl)-1-piperidinyl]butyl]-α-(hydroxymethyl)-α-butyl-benzeneacetic acid 4-[1-hydroxy-4-[4-(hydroxydiphenylmethyl)-1-piperidinyl]butyl]-α-(hydroxymethyl)-α-pentyl-benzeneacetic acid 4-[1-hydroxy-4-[4-(hydroxydiphenylmethyl)-1-piperidinyl]butyl]-α-(hydroxymethyl)-α-hexyl-benzeneacetic acid Examples of Synthesis Set Forth in Scheme B To a slurry of AlCl$_3$ (210 g, 1.6 mol) in methylene chloride (200 mL) cooled in an ice bath is added 4-chlorobutyryl chloride (121 g) dropwise while maintaining the pot temperature below 10° C. After 10 minutes, ethyl benzeneacetic acid (118 g, 0.72 mol) is added dropwise maintaining the pot temperature below 100° C. The mixture is stirred at room temperature for 1 hour, then heated to 40° C. After 4 hours, the solution is cooled to room temperature and poured onto crushed ice (2 L). Methylene chloride (1 L) is added. The organic phase is separated. The aqueous phase is extracted with two 1 L portions of methylene chloride. The combined organics are dried (MgSO$_4$) and concentrated. Toluene (1 L) is added and the solution is concentrated to ca. 500 mL. Ethanol (500 mL) is added. The solution is heated to 70° C. and HCl (g) is bubbled through for 20 minutes. The solution is sparged with N$_2$ and concentrated. Chromatography through silica gel (2.5 L) using an ethyl acetate/heptane gradient gives a 1:1 mixture of meta, para ethyl (4-chloro-1-oxobutyl)benzene acetic acid (119 g). To a slurry of LiOH (23.5 g, 0.56 mol) in water (100 mL) and ethanol (100 mL) is added the 1:1 mixture of meta, para ethyl (4-chloro-1-oxobutyl)benzene acetic acid (50 g, 0.19 mol). The reaction becomes exothermic and is cooled with an ice bath. After 1 hour, the solution is allowed to warm to room temperature. After 18 hours, the mixture is concentrated. Water (400 mL) and conc. HCl are added (until pH 4). Ethyl acetate (600 mL) is added. The organic phase is separated, washed with brine and dried (MgSO4).

The solution is heated on a steam bath and charcoal (ca. 3 g) is added. The mixture is filtered through Celite and concentrated. The residue is dissolved in ethyl acetate (300 mL) and heptane (600 mL) with heating. Seed crystals are added. After cooling an organic oil appears. Heptane (500 mL) is added and the mixture is heated to reflux, treated with charcoal (ca. 5 g), filtered and seeded. A solid forms and is collected. $^1$H NMR shows ca. 4:1 mixture of para:meta isomers. Recrystallization from ethyl acetate/heptane gives 4 (cyclopropylcarbonyl)benzeneacetic acid (4.3 g, 11%).

Examples of Synthesis As Set Forth in Scheme C

Step a: Preparation of 4-(cyclopropylcarbonyl) benzeneacetic acid, ethyl ester

See preparation under Step E, Scheme A, disclosed previously herein.

Step b: Preparation of [4-(cyclopropylcarbonyl)]-α-α-dimethylbenzeneacetic acid, ethyl ester In a 2 L, glass, jacketed reactor is loaded the 4-(cyclopropylcarbonyl) benzeneacetic acid, ethyl ester (232 g, 1 mole), diglyme (150 mL) and methyl chloride (127 g, 2.5 mole). In a heated addition vessel is loaded potassium tert-butoxide (182.4 g, 1.6 mole) and diglyme (1050 mL). The jacket for the reactor is set at −10° C. and the addition vessel contents are heated to 60° C. The base solution is added to the reactor at a rate which keeps the internal temperature of the reaction below 25° C. After the base addition, sodium ethoxide as a 21% solution in ethanol (86 g, 0.3 mole) is added to quench any excess methyl chloride. The entire reaction mixture is then agitated with toluene (900 mL) and water (1200 mL) containing sodium bicarbonate (8.4 g). The phases are separated and the organic layer is washed with additional water (200 mL) to remove any residual potassium chloride salts. Without phase separating, the entire solution is then acidified to pH=3 with concentrated HCl. The organic is then stripped of solvents to afford the title compound.

Step c: Preparation of 4-(4-chloro-1-oxobuty)-α,α-dimethylbenzeneacetic acid, ethyl ester To a 4 L reactor equipped with a gas inlet, overhead stirrer and temperature control, is charged [4-(cyclopropylcarbonyl)]-α,α-dimethylbenzeneacetic acid, ethyl ester (500 g). The oil is heated to 60° C. and the head space is evacuated. HCl is then added raising the pressure to 10 psig. After 4 hours, the excess HCl is vented and the oil is sparged with nitrogen for 5 minutes.

Step d: Preparation of Ethyl 4-[4-[4-(hydroxydiphenylmethyl)-1-piperidinyl]-1-oxobutyl]-α-α-dimethylbenzeneacetate hydrochloride According to the described procedure of Carr et al., U.S. Pat. No. 4,254,129, a mixture of 4.5 g (0.0163 mole) of α,α-diphenyl-4-piperidemethanol, 6.1 g (0.0205 mole) of ethyl 4-(4-chloro-1-oxobuty)-α,α-dimethylphenylacetate, 5 g (0.05 mole) of potassium bicarbonate and 0.05 g of potassium iodide in 50 ml of toluene is stirred and refluxed for 72 hours then filtered. Ether then ethereal hydrogen chloride is added to the filtrate, and the resulting precipitate collected and recrystallized several times from methanol-butanone and butanone to give ethyl 4-[4-[4-(hydroxydiphenylmethyl)-1-piperidinyl]-1-oxobutyl]-α,α-dimethylbenzeneacetate hydrochloride. M.P.205.5°–2081° C.

Step e: Preparation of Ethyl 4-[4[4-(hydroxydiphenylmethyl)-1-piperidinyl]-1-hydroxybutyl]-α,α-dimethylbenzeneacetate According to the described procedure of Carr et al., U.S. Pat. No. 4,254,129, a solution of 5.64 g (0.01 mole) of ethyl 4-[4[4-(hydroxydiphenylmethyl)-1-piperidinyl]-1-oxobutyl]-α,α-dimethylbenzeneacetate hydrochloride in 200 ml of absolute ethanol and 50 ml of methanol and 0.5 g of platinum oxide is hydrogenated at about 50 psi for about 1 hour until the infrared shows no evidence of a ketone carbonyl function. The solution is filtered and the filtrate concentrated leaving a residue which is recrystallized from butanone and methanol-butanone to give ethyl 4-[4[4-(hydroxydiphenylmethyl)-1-peperidinyl]-1-hydroxybuty]-α,α-dimethylbenzeneacetate HCl, M.P. 185°–187° C.

Step f: 4-[4[4-(Hydroxydiphenylmethyl)-1-piperidinyl]-1-hydroxybutyl]-α,α-dimethylbenzeneacetic acid According to the described procedure of Carr et al., U.S. Pat. No. 4,254,129, to a solution of 0.6 g of ethyl 4-[4[4-(hydroxydiphenylmethyl)-1-piperidinyl]-hydroxybutyl]-α,α-dimethylbenzeneacetate in 20 ml of absolute ethanol is added 10 ml of a 50% solution of sodium hydroxide. The mixture is refluxed for 3½ hours and concentrated to a solid after which a minimum amount of methanol to dissolve the residue is added. 10% Aqueous HCl is added until pH 7 is reached, the methanol removed by evaporation and water (25 ml) is added. The resulting precipitate is recrystallized from methanolbutanone to give 4-[4[4-(hydroxydiphenylmethyl)-1-piperidinyl]-1-hydroxybutyl]-α,α-dimethylbenzeneacetic acid, M.P. 195°–197° C.

The piperidine derivative of formula (I) is used according to the present invention as a histamine $H_1$-receptor antagonist and as such will provide relief of symptoms associated with histamine-mediated allergic disorders in patients suffering therefrom. Histamine-mediated allergic disorders are diseases or conditions which have a histamine-mediated allergic component such as, for example, seasonal allergic rhinitis, perennial rhinitis, idiopathic urticaria, asthma and the like. Relief of symptoms of an allergic disorder by treatment according to the present invention refers to a decrease in symptom severity over that expected in the absence of treatment and does not necessarily indicate a total elimination of the disease.

Antihistaminic potential is measured by affinity of a test compound for [$^3$H] pyrilamine binding sites associated with the antagonist component of $H_1$-histaminergic receptors in animal brain membranes. Affinity for this receptor is indicative of the potential of a test compound to interact with central and peripheral $H_1$-histaminergic receptors.

The following method is used to determine the affinity of test compounds for [$^3$H] pyrilamine binding sites in rat cortex.

The brains of young male rats are removed. The cortici are dissected and stored at −20° C. or immediately used. The tissue is homogenized in 10 ml of ice-cold 50 nM K/NaPO$_4$ buffer (pH 7.4) using a Polytron (setting 6 for 15 seconds). The homogenate is centrifuged at 40,000 g for 15 minutes at 4° C. The pellet is resuspended in the same buffer in order to have 100 mg wet weight/ml buffer. The incubation tubes contain 50 mM K/NaPO$_4$ buffer, promethazine (2.10–6M final) or test compound, $^3$H pyrilamine (2 nM final) and homogenate (10 mg wet weight per tube) in a final volume of 250–1000 ml. After a 30 minute incubation at room temperature each incubation is terminated by rapid filtration through Whatman GF/B glass fiber filters, presoaked in water when using a Brandel cell harvester, or used as such when the filtration is performed with a 96 well Skatron cell harvester. The filters are rinsed with 3×3 ml 0.9% NaCl (Brandel) or prewetted and rinsed for 10 sec with NaCl (Skatron). The filters are either transferred to scintillation vials and 10 ml Quicksafe A is added for liquid scintillation spectrometry or a thin layer of solid scintillant is melted onto the filters and the filters then counted using a betaplate beta counter. Specific binding of $^3$H pyrilamine is measured as the excess over blanks taken in the presence of $2.10$–$6$ M promethazine. Protein content of the membranes is determined by the method of Lowry et al., *J. Biol. Chem.* 193, 265–275 (1951). Displacement curves are analyzed using the GraphPad (GraphPad Software, Inc.) or similar program to obtain Hill slopes and $IC_{50}$ values. The $K_i$ value is then determined with the Cheng-Prusoff equation described by Cheng et al., in *Biochem. Pharmacol.*, 22, 3099–3108 (1973), using the $K_D$ for $^3$H pyrilamine as obtained from previous saturation experiments performed under the same conditions.

The $K_i$ for 4-[1-hydroxy-4-[4-(hydroxydiphenylmethyl)-1-piperidinyl]butyl]-α-(hydroxymethyl)-α-methyl-benzeneacetic acid is $3.6 \times 10^{-7}$ indicating that the piperidine derivative of formula (I) is useful for the treatment of histamine-mediated allergic disorders.

As used herein, the term "patient" refers to an adult person who is suffering from a histamine-mediated allergic disorder. It is understood that for purposes of the present invention, the term "adult" refers to a person of 12 years of age or older who would typically be treated for allergic disorders with an antihistamine dosage as recommended for adults.

The identification of those patients who would benefit from the present invention is well within the ability and knowledge of one skilled in the art. A clinician skilled in the art can readily identify, by the use of clinical tests, physical examination and medical/family history, those patients who are suffering from an allergic disorder that is histamine-mediated.

The quantity of novel compound administered will vary depending on the mode of administration and can be any effective antiallergic amount. The quantity of novel compound administered may vary over a wide range to provide in a unit dosage an effective amount of from about 0.01 to 20 mg/kg of body weight of the patient per day to achieve the desired effect. For example, the desired antihistamine, antiallergy and bronchodilator effects can be obtained by administering the piperidine compound of formula (I) to a patient in a daily amount of from about 10 mg to about 50 mg. A preferred daily dose is from about 20 mg to about 40 mg. The most preferred daily dose is about 30 mg.

It is of course understood that the daily dose may be administered to a patient according to a dosage regimen in single or multiple dosage units. For example, a daily dose may be administered in a regimen requiring one, two, three, or four unit doses. Typically, these unit doses will be of equal strength and will be administered on a time schedule so that each dose is approximately equally spaced throughout the day. For example, a daily dose requiring a once a day dosage regimen may be administered about every 24 hours; a daily dose requiring a twice-a-day dosage regimen may be administered about every 12 hours; a daily dose requiring a three times-a-day dosage regimen may be administered about every 8 hours; a daily dose requiring a four times-a-day dosage regimen may be administered about every 6 hours.

The piperidine derivative of formula (I) can be administered according to the present invention in any form or mode which makes the compound bioavailable in effective amounts, including oral and parenteral routes. For example, the piperidine derivative of formula (I) can be administered orally, subcutaneously, transdermally, intranasally, and the like. Oral administration is preferred. One skilled in the art of preparing formulations can readily select the proper form and mode of administration depending upon the particular characteristics of the compound selected, the disease state to be treated, the stage of the disease, and other relevant circumstances.

The compounds can be administered alone or in the form of a pharmaceutical composition with pharmaceutically acceptable carriers or excipients, the proportion and nature of which are determined by the chosen route of administration and standard pharmaceutical practice. The piperidine derivative of formula (I), while effective itself, may be formulated and administered in the form of its pharmaceutically acceptable acid addition salt for purposes of stability, convenience of crystallization, increased solubility and the like. In addition, an individual polymorph, solvate, or individual stereoisomer of the piperidine derivative of formula (I) [i.e., (R,R)-4-[1-hydroxy-4-[4-(hydroxydiphenylmethyl)-1-piperidinyl]butyl]-α-(hydroxymethyl)-α-methyl-benzeneacetic acid; (R,S)-4-[1-hydroxy-4-[4-(hydroxydiphenylmethyl)-1-piperidinyl]butyl]-α-(hydroxymethyl)-α-methyl benzeneacetic acid; (S,S)-4-[1-hydroxy-4-[4-(hydroxydiphenylmethyl)-1-piperidinyl]butyl]-α-(hydroxymethyl)-α-methyl-benzeneacetic acid and (S,R)-4-[1 hydroxy-4-[4-(hydroxydiphenylmethyl)-1-piperidinyl]butyl]-α-(hydroxymethyl)-α-methyl-benzeneacetic acid] may be used.

The present invention contemplates compositions comprising the piperidine derivative of formula (I) in admixture or otherwise in association with one or more inert carriers. These compositions are useful, for example, as assay standards, as convenient means of making bulk shipments, or as pharmaceutical compositions. An assayable amount of the piperidine derivative of formula (I) is an amount which is readily measurable by standard assay procedures and techniques as are well known and appreciated by those skilled in the art. Assayable amounts of the piperidine derivative of formula (I) will generally vary from about 0.001% to about 75% of the composition by weight. Inert carriers can be any material which does not to degrade or otherwise covalently react with the piperidine derivative of formula (I). Examples of suitable inert carriers are water; aqueous buffers, such as those which are generally useful in High Performance Liquid Chromatography (HPLC) analysis organic solvents, such as acetonitrile, ethyl acetate, hexane and the like; and pharmaceutically acceptable carriers or excipients.

More particularly, the present invention contemplates a pharmaceutical composition in solid unit dosage form comprising an amount of the piperidine derivative of formula (I) from about 15 mg to about 30 mg in admixture with a pharmaceutically acceptable carrier. As used herein, the term "solid unit dosage form" contemplates a solid dosage form for oral administration such as a tablet, capsule, and the like, as well as solid dosage forms for parenteral administration such as a transdermal patch, and the like.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, solutions, suspensions, transdermal patch, and the like.

The piperidine derivative of formula (I) may be administered orally, for example, with an inert diluent or with an edible carrier. It may be enclosed in gelatin capsules or compressed into tablets. For the purpose of oral therapeutic administration, the piperidine derivative of formula (I) may be incorporated with excipients and used in the form of tablets, capsules, elixirs, suspensions, syrups, wafers, chewing gums and the like. These preparations should contain at least 4% of the compound of the invention, the active ingredient, but may be varied depending upon the particular form and may conveniently be between about 4% to about 70% of the weight of the unit. The amount of the compound present in compositions is such that a suitable dosage will be obtained upon administration. Preferred compositions and preparations according to the present invention are prepared so that an oral unit dosage form contains between about 15 mg to about 30 mg. Most preferred unit doses for oral administration are those which contain about 15 mg to about 30 mg.

The tablets, pills, capsules, and the like may also contain one or more of the following adjuvants: binders such as microcrystalline cellulose, gum tragacanth or gelatin; excipients such as starch or lactose, disintegrating agents such as alginic acid, Primogel™, corn starch, carbonate salts such as sodium bicarbonate or calcium carbonate, and the like; lubricants such as magnesium stearate or Sterotex™; glidents such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used. Preferred excipients are corn starch, gelatin, lactose, magnesium stearate and sodium bicarbonate.

Oral unit dosage forms may be formulated to provide immediate or sustained release characteristics. These forms may be formulated according to conventional techniques and procedures to give the desirable dissolution and bioavailability characteristics.

In addition, the piperidine derivative of formula (I) may be incorporated into a solution or suspension for oral or parenteral administration. These preparations should contain at least 0.1% of the piperidine derivative of formula (I), but may be varied to be between 0.1 and about 50% of the weight thereof. The amount of the piperidine derivative of formula (I) in such compositions is such that a suitable dosage will be obtained upon oral or parenteral administration.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose.

Transdermal dosage forms for administering the piperidine derivative of formula (I) can be prepared by conventional techniques well known in the art of pharmaceutical science such as by incorporating the piperidine derivative of formula (I) into various polymeric reservoir matrix materials. These polymeric matrix materials may include pressure sensitive acrylic, silicone, polyurethane, ethylene vinyl acetate copolymers, polyolefins, and rubber adhesive matrices, medical grade silicone fluids, and medical grade silicone elastamers, which are well known in the art for forming reservoirs for transdermal delivery of drugs.

It is further contemplated that the piperidine derivative of formula (I) according to the present invention, may be formulated with a variety of other active ingredients which are commonly combined with antihistamines, such as a decongestant, including pseudoephedrine and the like; analgesics such as acetaminophen and the like, non-steroidal anti-inflammatory agents such as ibuprofen and the like.

What is claimed is:

1. A compound of the formula

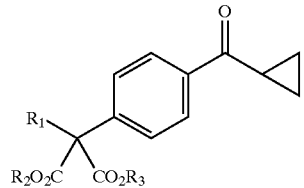

wherein $R_1$ is H or $C_1$–$C_6$alkyl and the $C_1$–$C_6$alkyl moiety is straight or branched;

$R_2$ and $R_3$ are each independently $C_1$–$C_6$alkyl and the $C_1$–$C_6$alkyl moiety is straight or branched; or stereoisomers thereof.

2. The compound of claim 1 wherein $R_1$ is methyl and $R_2$ and $R_3$ are ethyl.

* * * * *